United States Patent
Plodinec et al.

(10) Patent No.: US 8,756,711 B2
(45) Date of Patent: Jun. 17, 2014

(54) METHOD FOR STAGING CANCER PROGRESSION BY AFM

(75) Inventors: Marija Plodinec, Basel (CH); Roderick Lim, Riehen/Basel (CH); Marko Loparic, Basel (CH)

(73) Assignee: Universitat Basel, Basel (CH)

( * ) Notice: Subject to any disclaimer, the term of this patent is extended or adjusted under 35 U.S.C. 154(b) by 0 days.

(21) Appl. No.: 13/992,743

(22) PCT Filed: Dec. 12, 2011

(86) PCT No.: PCT/EP2011/072494
§ 371 (c)(1),
(2), (4) Date: Sep. 15, 2013

(87) PCT Pub. No.: WO2012/076729
PCT Pub. Date: Jun. 14, 2012

(65) Prior Publication Data
US 2014/0007309 A1 Jan. 2, 2014

Related U.S. Application Data

(60) Provisional application No. 61/421,655, filed on Dec. 10, 2010.

(51) Int. Cl.
*G01Q 60/00* (2010.01)
(52) U.S. Cl.
USPC .................. 850/63; 850/21; 850/33; 850/62
(58) Field of Classification Search
USPC ........................................ 850/21, 33, 62, 63
See application file for complete search history.

(56) References Cited

FOREIGN PATENT DOCUMENTS

WO WO 2005/003290 1/2005

OTHER PUBLICATIONS

Cross et al, "AFM-based analysis of human metastatic cancer cells", Nanotechnology, vol. 19, Sep. 24, 2008, pp. 1-8.
Loparic et al, "Micro-and nanomechanical analysis of articular cartilage by indentation-type atomic force microscopy: Validation with a gel-micofiber composite", Biophycial Journal, vol. 98, Jun. 1, 2010, pp. 2731-2740.
Samani et al, "An inverse problem solution for measuring the elastic modulus of intact ex vivo breast tissue tumours", Physics in Medicine and Biology, vol. 52, Mar. 7, 2007, pp. 1247-1260.

*Primary Examiner* — Michael Maskell
(74) *Attorney, Agent, or Firm* — JMB Davis Ben-David

(57) ABSTRACT

The present invention relates to a method for classifying a tissue biopsy sample obtained from a tumor, comprising determining a plurality of stiffness values for said sample by measuring a plurality of points on the sample with a spatial resolution of at least 100 μm and assigning the sample to a probability of malignancy. A sample showing a unimodal stiffness distribution is assigned to a high probability of being non-malignant, and a sample showing an at least bimodal stiffness distribution is assigned to a high probability of being malignant, wherein said stiffness distribution is characterized by a first peak exhibiting an at least two-fold higher stiffness value than a second peak. The present invention further relates to a system for classifying a tumor tissue biopsy sample.

16 Claims, 18 Drawing Sheets

METHOD FOR STAGING CANCER PROGRESSION BY AFM

CROSS-REFERENCE TO RELATED APPLICATIONS

This is the U.S. National Stage of International Application No. PCT/EP2011/072494, filed Dec. 12, 2011, which was published in English under PCT Article 21(2), which in turn claims the benefit of U.S. Provisional Patent Application No. 61/421,655, filed Dec. 10, 2010.

The present invention relates to a method and a system for staging cancer progression of a tumour.

The cytoskeleton, a supramolecular network comprised of actin filaments, intermediate filaments and microtubules, is dynamically remodelled during cell adhesion, migration, proliferation and differentiation. Many of these fundamental cellular processes are modulated by mechanical forces. Correspondingly, tumour genesis, which results from changes in these fundamental processes, is associated with alterations in biomechanics.

Atomic force microscopy (AFM) has been used to probe the mechanical properties of isolated cancer cells. Cell elasticity and deformability have been recognized as a marker for the phenotypic consequences of alterations in cytoarchitecture and adhesion that are associated with malignant transformation. However, stiffness was measured at one specific site only, and thus does not appropriately reflect the structural heterogeneity of a cell. Also the absence of the native tissue environment is likely to have an influence on the mechanical behaviour.

Force changes that arise from interactions with the microenvironment play a significant role in triggering genetic changes that induce tumour genesis. It has been shown that the mechanical properties of living cells are highly dependent on many factors present in their three-dimensional (3D) microenvironment. Studies performed on 3D mammary cell cultures and mouse mammary glands have suggested that increased matrix deposition and cross-linking consistent with ECM stiffening promotes the development and progression of cancer. In this case, cancer detection has been achieved by unconfined compression of the whole mammary gland. However, this approach only considered the peripheral region of the tumour, while the bulk of the underlying cancer was not accessible for testing.

The relative stiffening of the peripheral tumour stroma compared to the adjacent normal mammary gland tissue has led to the widespread assumption that breast cancer is stiffer than the normal mammary gland tissue or benign lesions. The inconsistency of stiffness data obtained from individual cells in culture and from tissues in situ emphasizes the importance of taking into account both the measuring approaches, but even more other microenvironmental factors that are present in a 3D tissue context.

Additionally, a variety of biochemical gradients develops during tumour development and progression within the tissue. Oxygen and pH are considered as the key microenvironmental factors in the development and growth of tumours and their response to treatment. For instance, hypoxia, as a constituent of the tumour cell microenvironment, is a prominent feature of malignant tumours, modifying the pathways that regulate cell proliferation, angiogenesis and cell death.

Mechanical properties of cancer cells and tissues, however, have not yet been evaluated in the context of hypoxia. The tools applied so far have either included mechanical measurements of extracted cancer cells from the primary tissue or just measured tumour periphery, which has provided limited insight into the structural and mechanical heterogeneity of a tumour tissue.

The objective of the present invention is to provide methods and means for staging cancer progression of a tumour.

The present invention was made during the course of an investigation assessing the nanomechanical properties of tumour biopsy samples by AFM. It was surprisingly found that human and murine cancer tissues exhibit a gradual softening from the tumour periphery (extracellular matrix) to the core (cancer cells) while stromal tissue at the tumour periphery is stiffer than the underlying tumour. Another surprising finding was that this tissue softening correlates with tumour hypoxia.

DEFINITIONS

Stiffness or elasticity in the sense of the invention means the resistance of a tissue sample or tissue to deformation by an applied force. The stiffness or elasticity is measured as the elastic modulus of the tissue sample in Pascal (Pa). A soft tissue sample is characterized by a low stiffness value and a rigid tissue is characterized by an elevated stiffness value.

Such deformation force may be applied to the tissue sample or tissue by a stylus (as part, for example, of an atomic force microscope) that impinges the tissue sample or tissue, wherein either the stylus or the tissue sample is moved in a vertical direction relative to each other. To measure a plurality of points on a sample, the stylus or the sample may be additionally moved in a lateral direction, wherein a lateral direction in the sense of the invention means a direction that is orthogonal to the vertical direction.

The stylus may be a cantilever with a sharp tip or an attached colloidal particle that acts as a probe. A cantilever in the sense of the invention means a beam or arm that is anchored at only one end. Deflections of the cantilever caused by repulsive or attractive forces between the sample surface and the tip may be optically detected, for example by an interferometer or by a laser focused on the cantilever's back, and reflected onto a split photodiode, wherein the photodiode registers the deflection of the cantilever as a voltage difference, which can be converted into nanometers. Alternatively, the deflection of the cantilever may be detected by a piezoelectric sensor, wherein the strain of the cantilever is converted into an electrical charge.

An area in the sense of the invention refers to an area that is defined by a grid of (measurement) points, wherein each point corresponds to indentation footprint of the stylus as described above and each point is not more than 100 µm, preferably 50 µm, 20 µm, 10 µm or 1 µm away from its next point. By way of non-limiting example, an area has a size of 25 µm$^2$, 50 µm$^2$, 100 µm$^2$, 200 µm$^2$, 300 µm$^2$, 400 µm$^2$, 500 µm$^2$, 600 µm$^2$, 750 µm$^2$, 1000 µm$^2$, 5000 µm$^2$ or 10.000 µm$^2$ and the geometrical centre points of two areas are at least 100 µm, 200 µm, 300 µm, 400 µm, 500 µm or 1 mm apart.

Measured force and indentation depth for any given sample depend on the cantilever spring constant and tip radius.

Spatial resolution in the sense of the invention means the minimal distance between two points on a tissue or tissue sample by which the two points can be discriminated regarding their stiffness. A spatial resolution of at least 1 mm, preferably 100 µm, 10 µm or 1 µm means that the maximal distance by which two points still can be discriminated is 1 mm, preferably 100 µm, 10 µm or 1 µm. A spatial resolution of at least 100 µm, preferably 10 µm or 1 µm also encompasses higher resolutions. A resolution higher than 1 µm means two points having a distance smaller than 1 µm still can be discriminated. Examples of resolutions higher than 100 µm are 10 µm and 1 µm. Examples of resolutions higher than 1 µm are 0.5 µm, 0.1 µm and 10 nm.

A tissue biopsy sample in the sense of the invention refers to a tissue sample that is obtained by a biopsy and comprises contiguous cells and extracellular matrix.

Biopsy in the sense of the invention means a method for removal of a tissue part or a tissue for examination. Such biopsy may a needle aspiration biopsy, a punch biopsy, a vacuum-assisted core biopsy, a core needle biopsy or a forceps biopsy. The removal may be performed with the help of suitable tools such as a hollow needle, a round sharp knife or a scalpel. A tissue biopsy sample may additionally be obtained by endoscopes or endoscopic methods.

The biopsy may be guided by a suitable method such as ultrasound or CT (X-ray computed tomography), wherein a tumour or a conspicuous lesion can be detected or located.

Normal tissue in the sense of the invention means an ensemble of contiguous cells with identically physiological function that are characterized by a normal, controlled growth and normal cellular function.

A tumour in the sense of the invention means a neoplasm or a lesion that is formed by an abnormal growth of neoplastic cells. The tumour can be benign, premalignant or malignant. The classification of a tissue biopsy samples from a human mammary carcinoma is preferred. A benign lesion or tumour in the sense of the invention refers to a tumour that lacks the ability to metastasize.

Malignancy or "a malignant tumour" in the sense of the invention means the ability of a tumour to penetrate the basal membrane, invade neighbouring tissues or spread through the body. A malignant tumour is synonymous with a malignant neoplasm or cancer, in particular with invasive cancer.

A stiffness distribution in the sense of the invention means frequency of different stiffness values determined from an individual tissue biopsy sample. A determined stiffness distribution may additionally be fitted to a Gaussian function. A unimodal stiffness distribution is a distribution of discrete stiffness values having a single maximum, which indicates a sample having a uniform stiffness. A bimodal distribution function has two maxima. Such distribution may be caused by a sample having two differently stiff parts, for example a soft tumour core and a stiff periphery. A trimodal stiffness distribution in the sense of the invention means a distribution characterized by three local maxima. A trimodal distribution may indicate that normal tissue, a border region characterized by hard stroma and a soft tumour core have contributed to the values making up the distribution. A sample at least bimodal stiffness distribution has a bimodal, trimodal or n-modal (with n being an integer >1) distribution function.

A plurality in the sense of the invention means at least 5, 7, 8, 9, 10, 20, 30, 40, 50, 100, 200, 300, 400, 500 or 1000 values.

According to a first aspect of the invention, an ex vivo method for classifying a tissue biopsy sample obtained from a tumour is provided, comprising the steps:
determining a plurality of stiffness values of the tumour biopsy sample by measuring a plurality of points on the sample with a spatial resolution of at least 100 µm, preferably 50 µm, 20 µm, 10 µm or 1 µm, and
assigning the sample to a probability of malignancy.

According to one alternative of this aspect of the invention, the method for classifying a tissue biopsy sample obtained from a tumour comprises determining the stiffness values for a plurality of points on said sample with a spatial resolution of at least 100 µm, preferably 50 µm, 20 µm, 10 µm or 1 µm, resulting in a stiffness distribution, and assigning said sample to a probability of malignancy on the basis of this stiffness distribution, whereby a sample showing an unimodal stiffness distribution is assigned to a high probability of being normal or non-malignant tissue, and a sample showing an at least bimodal stiffness distribution is assigned to a high probability of being malignant tissue.

According to another alternative of this first aspect of the invention, an ex vivo method for classifying a tissue biopsy sample obtained from a tumour is provided, comprising the steps:
determining a plurality of stiffness values of the tumour biopsy sample for points in an area, said points forming a grid of $n_1$ by $n_2$ points ($n_1$ and $n_2$ independently being integers >1) with a spatial resolution of at least 100 µm, preferably 10 µm or 1 µm, and
assigning the sample to a probability of malignancy.

According to one embodiment of this latter alternative, a grid of 5 by 5 points (resulting in 25 points), 7 by 7 points, 10 by 10 points, 15 by 15 points, 20 by 20 points, 50 by 50 points or 100 by 100 points are measured for one area. Each point therein is a certain distance spaced apart from the next point, the spacing of the points representing the resolution. According to one embodiment, the resolution is 100 µm; according to another embodiment, the resolution is 50 µm, 20 µm, 10 µm or 1 µm. A resolution of 1 µm, for example, in a grid of 50 by 50 points results in an area of 2500 µm².

According to another embodiment, two, three or four such areas or grids are measured, each grid or area representing a region of the biopsy, wherein the distance of the centre point or geometrical centre of one grid or area to the next are 100 µm, 250 µm, 500 µm or 1 mm. In one embodiment, the geometrical distance of the centre point of one grid to the next is a multiple of at least 10, 25, 50, 100 or 250 of the spatial resolution of the points in the grid.

According to one aspect of the invention, a method for classifying a tissue biopsy sample obtained from a tumour is provided, comprising
determining a plurality of stiffness values for said sample by measuring a plurality of points on the sample with a spatial resolution of at least 100 µm, preferably 10 µm or 1 µm, and
assigning the sample to a probability of malignancy,
wherein
a sample showing a unimodal stiffness distribution is assigned to a high probability of being non-malignant, and
a sample showing an at least bimodal stiffness distribution is assigned to a high probability of being malignant, wherein said stiffness distribution is characterized by a first peak exhibiting an at least two-fold higher stiffness value than a second peak.

For determining stiffness values with a spatial resolution of at least 1 µm, 2 µm, 5 µm, 7 µm, 10 µm or 100 µm the stylus or sample may be moved with submicrometer or micrometer precision in both vertical and lateral directions, which means in steps of not larger than 1 µm, 2 µm, 5 µm, 7 µm, 10 µm or 100 µm. In some embodiments of the aspects of the invention defined below, the tissue sample is mounted on a sample support such as a piezo electric actuator that can be moved both vertical and lateral direction with an submicrometer or micrometer precision. Alternatively, the tissue sample is mounted on a sample support such as a petri dish or a glass slide, wherein the petri dish or the glass slide is mounted on the piezoelectric element described above.

The stiffness or elasticity of a sample may be determined by measuring the force necessary to impress the stylus into the tissue sample to a definable indentation depth. Alternatively, the stiffness may be determined by measuring the indentation depth of the stylus pressed into the tissue sample with a definable force.

According to one embodiment, the indentation footprint of the stylus on the tissue sample is not larger than 1, 2, 9, 16 or 25 µm², wherein the indentation footprint corresponds to an individual point of the plurality of points described in the above aspect of the invention.

According to one embodiment, the cantilever has a spring constant of 0.01 Nm⁻¹, 0.025 Nm⁻¹, 0.05 Nm⁻¹, 0.06 Nm⁻¹, 0.075 Nm⁻¹, 0.1 Nm⁻¹, 0.15 Nm⁻¹, 0.2 Nm⁻¹, 0.25 Nm⁻¹, 0.3 Nm⁻¹, 0.5 Nm⁻¹, 0.75 Nm⁻¹, 1 Nm⁻¹ or 10 Nm⁻¹.

According to one embodiment, the radius of the tip is 0.01 µm, 0.02 µm, 0.05 µm, 0.07 µm, 0.1 µm, 0.5 µm, 1 µm, 1.5 µm, 2 µm, 2.5 µm, 3 µm, 3.5 µm, 4 µm, 4.5 µm or 5 µm.

In one embodiment, the cantilever spring constant, k, and the stiffness of the sample are of similar magnitude. This results in optimal sensitivity.

According to one embodiment, a force applied to the tissue sample has a value of 0.05 nN, 0.1 nN, 1 nN, 2 nN, 3 nN, 4 nN, 5 nN, 6 nN, 7 nN, 8 nN, 9 nN, 10 nN, 100 nN, 1000 nN, 10,000 nN, 100,000 nN, and the indentation depth applied to the tissue sample is 100 nm, 300 nm, 500 nm, 700 nm, 1000 nm, 1300 nm, 1500 nm, 1700 nm, 2000 nm, 2200 nm, 2500 nm, 2700 nm, 3000 nm, 3200 nm, 3500 nm, 3700 nm, 4000 nm, 4500 nm, 5000 nm, 5500 nm or 6000 nm.

According to one embodiment, the stiffness is calculated from the slope of force-displacement curves, wherein the cantilever is indented into the sample surface with a definably force and retracted one or several times, and the resulting deflection of the cantilever is determined in dependence of the tip-sample distance.

According to certain embodiments of the invention, a sample showing a unimodal stiffness distribution is assigned to a high probability of being non-malignant, and a sample showing an at least bimodal stiffness distribution is assigned to a high probability of being malignant.

In other words, a sample characterized by a unimodal stiffness distribution can be assigned to a low probability of representing a malign tumour, however to assess whether such sample represents normal tissue or a precancerous lesion, the absolute stiffness of the sample may have to be taken into account. A benign lesion generally shows a higher stiffness compared to normal tissue. In one embodiment, a unimodal distribution representing a benign lesion has a peak value (representing the greatest number of measurement points in the distribution function) of about 1.3 to 2 times the peak value for normal tissue of the same tissue source.

A bimodal stiffness distribution likely represents a malignant tumour, where a soft region contributes to an abundance of low stiffness values and a rigid periphery has stiffness value larger than normal tissues. A sample showing trimodal or higher modal stiffness distribution may be assigned to a high probability representing malignant tumour or a mixture of normal tissue, a benign lesion and/or a malignant tumour.

According to one embodiment of the invention, the biopsy tissue sample is obtained from human mammary carcinoma or a metastasis from a lymph node, from the lungs, a bone metastasis, a liver metastasis, a brain metastasis or other breast carcinoma metastasis related tissues.

According to one embodiment of the invention, a sample showing an at least bimodal stiffness distribution is assigned to a high probability of being malignant, wherein said stiffness distribution is characterized by a first peak exhibiting an at least two-fold higher stiffness value than a second peak.

According to one embodiment, the plurality of points is arranged as a grid of $n_1$ by $n_2$ points, the grid defining an area, $n_1$ and $n_2$ independently being integers >1.

According to one embodiment, the tumour is a human mammary carcinoma or a lymph node, lung, bone, liver or, brain metastasis.

According to one embodiment, a grid of 5 by 5 points (resulting in 25 points), 7 by 7 points, 10 by 10 points, 15 by 15 points, 20 by 20 points, 50 by 50 points or 100 by 100 points are measured for one area. In one preferred embodiment, the area is defined of a grid of 24×24 points with a size of 400 µm².

According to one embodiment, the stiffness values of at least two different areas of the same sample are determined, and the distance between the geometrical centres of said areas is a multiple of the spatial resolution, said multiple being at least 10 times the spatial resolution. According to a preferred embodiment, the multiple is 20, 30 or 50.

According to one embodiment of the invention, the biopsy tissue sample is a biopsy of >5 µm in diameter or thickness and may be obtained by collecting the biopsy with a hollow needle. According to one embodiment, the biopsy tissue sample is a cylindrical or prismatic biopsy with a diameter of at least 0.5 mm. In one embodiment, the biopsy sample is a cylindrical or prismatic biopsy representing at least one half of the cross-section of the tumour described above and exhibiting a distinct orientation from core to periphery of the tumour, and the areas of the biopsy sample are positioned on the surface of sample along the sample's longitudinal axis over a distance of 1 mm, 2 mm, 3 mm, 4 mm, 5 mm, 6 mm, 7 mm, 8 mm, 9 mm, 10 mm, 15 mm or 20 mm.

More preferably, the three-dimensional integrity and heterogeneity of the obtained sample is preserved after collection and the tissue sample exhibits a distinct orientation from core to periphery of the tumour.

According to another embodiment of the invention, the determination of the stiffness values is performed under physiological conditions.

Physiological conditions in the sense of the invention refers to conditions necessary to preserve the structural integrity and mechanical properties of the biopsy tissue sample, maintaining viability of the tissue by any chemicals or physical agents and include in particular that after collection the sample is stored in a physiological buffer such as phosphate buffered saline or Ringer solution, and stiffness determination is performed at 20, 25, 30 or 37° C. The Ringer solution may further be supplemented with glucose and a protease cocktail. Further, stiffness determination of the biopsy tissue sample may be performed within 1 h, 2 h, 6 h, 12 h, 24 h, 48 h or 72 h after collection without changing the mechanical properties of the sample. "Physiological conditions" particularly do not comprise frozen tissue or thawed tissue, or paraffin-embedded samples.

According to another preferred embodiment of the invention, the stiffness of a mammary biopsy sample is determined and
 a sample showing a stiffness distribution characterized by a between 1.1 kPa and 1.85 kPa is assigned to a high probability of being a normal mammary tissue,
 a sample showing a stiffness distribution characterized by a between 1.9 kPa and 3.7 kPa is assigned to a high probability of being a benign lesion, and
 a sample showing a stiffness distribution characterized by peaks between 0.31 kPa and 0.75 kPa and at a value larger than 1.2 kPa is assigned to a high probability of being a malignant tumour.

According to one embodiment, a sample showing a stiffness distribution characterized by peaks at between 0.31 kPa and 0.75 kPa and 1.2 kPa and 2.0 kPa is assigned to a high probability of being a malignant tumour.

A peak in the sense of the invention refers to a local maximum in the stiffness value distribution and signifies the stiffness value with the highest frequency within a sample, or within the immediate neighboring values.

According to one embodiment, determining of a plurality of stiffness values is performed by measuring at least 5 areas, 10 areas, 15 areas, 20 areas, 25 areas or 30 areas of the biopsy sample, wherein the area is defined as above. For example, the longitudinal axis of the sample may be represented by a string of areas as laid out above.

For rough samples, problems can occur when the corrugations (sample unevenness in the z-axis) of the sample surface on the scanning area are larger than the range of the given nanoscanner in the z-axis (with current set-ups, usually 5 μm to 100 μm). If the corrugations are too large, the piezo element will either extend or retract completely. The probe or cantilever will lose contact if the piezo element is fully extended but the sample surface is still descending. On the other hand, the force of the cantilever will increase over the given force maximum if the piezo element is already fully contracted but the sample surface is still ascending. The cantilever tip is then literally pressed into the sample surface. In both cases, the above mentioned constant tip-sample force is not maintained.

According to one embodiment, the stiffness values are determined by a scanning probe microscope. This device has a probe or cantilever (2) with a tip (21) for interacting with said sample (4), and additionally comprises a nanoscanner (1) for retaining said sample (4) or said probe or cantilever (2). The extension of said nanoscanner (1) along a first direction (R), along which said tip (21) is moved towards said sample (4), is monitored. A level of said probe or cantilever (2) along said first direction (R) is adjusted by means of an additional actuator (3) when said nanoscanner (1) exhibits an extension below or above a threshold value.

According to one embodiment, the scanning probe microscope has a resolving power of at least 1 μm. Resolving power in the sense of the invention refers to the minimal distance between points by which a scanning probe microscope is still able to discriminate between two points on a sample regarding their probed characteristics such as charge, magnetisation or a mechanical property. A resolving power of at least 1 μm means that the microscope is able to discriminate two points that are not more than 1 μm apart. A resolving power of at least 1 μm also encompasses higher resolving powers. A resolving power higher than 1 μm means that the microscope can discriminate two points having a distance smaller than 1 μm. Examples of resolving powers higher than 1 μm are 0.5 μm, 0.1 μm, 10 nm and 1 nm.

The adjustment of a level of the probe along the first direction is configured to prevent the probe's tip from coming to close to the sample or from being to far way from the sample. The adjusting may be performed by lowering or lifting the probe or lowering a lifting the sample along the first direction.

A nanoscanner in the sense of the invention refers to a device for moving the sample or the probe with sub-micrometer or at least micrometer precision along the first direction described above. Such nanoscanner may be a piezo element or a linear motor such as voice coil motor.

A piezo element in the sense of the invention refers to a body composed of a piezoelectric material that can be deformed by application of an electric current. Such piezo element is extendable and retractable along at least one direction. Further, the piezo element may be made of a suitable material such as crystal or ceramics, for example quartz, barium titanate, lead titanate, sodium tungstate, sodium niobate, lead zirconate titanate or bismuth ferrite and may be extendable or retractable within a range of 5, 10, 15, 20, 25, 30, 35, 40, 50, 60, 70, 80, 90 or 100 μm.

A voice coil motor in the sense of the invention refers to a motor comprising a magnetic housing and an electromagnetic coil that are movable in each other. Such magnetic housing may comprise a permanent magnet in a housing composed of iron. Such electromagnetic coil comprises a conductive wire wound around a core. The voice coil motor may additionally comprise a flexure hinge structure which may be used as a spring between the probe and the housing. The application of a voltage across the terminals of the motor causes the motor to move to one direction, while reversing the polarity of the applied voltage will move the motor to the opposite direction. The extension of a voice coil motor in the sense of the invention refers to its stroke or lift, wherein the maximal extension refers to the maximal stroke or lift and the minimal extension to zero stroke or lift.

Further, the nanoscanner may be directly coupled to the probe or to the probe assembly (TOP-DOWN setup, see FIG. 16). Alternatively, the nanoscanner may be directly coupled to the sample or the sample holder (BOTTOM-UP setup, see FIG. 17). Directly coupling in the sense of the invention refers to a physical connection between the nanoscanner and the probe, the probe assembly, the sample or the sample holder, wherein the physical connection is configured to enable the nanoscanner to move the probe, probe assembly, sample of sample holder in at least the first direction as described above. The nanoscanner may be further configured to move the probe, probe assembly, sample or sample holder in the second and third direction described above.

The threshold value corresponds to the optimal working range of the nanoscanner, in particular of a piezo element, depending on construction, design or used material of the nanoscanner. In particular, the threshold value may correspond to the upper and lower limit of the nanoscanner's optimal working range.

An actuator in the sense of the invention means a device for moving or controlling a mechanism or system different from the piezo element described above and which converts energy into motion. Such actuator may be operated by a source of energy such as electric current, hydraulic fluid pressure or pneumatic pressure. Examples for an actuator are, without being restricted to, a pneumatic actuator, a hydraulic actuator, a piezoelectric actuator, a comb drive, a linear actuator or motor, an electroactive polymer or an electric motor such as servo motor, stepper motor or voice coil motor.

According to one embodiment, the nanoscanner is designed, with respect to its extension, to maintain a constant probe tip-sample interaction force. Such force has been described above.

According to another embodiment, the extension of the nanoscanner is configured to maintain a constant probe tip-sample distance.

According to another embodiment, the extension of the nanoscanner is configured to maintain a constant indentation depth of the probe tip into the sample.

According to one embodiment, monitoring the extension of the nanoscanner according to the aspect and embodiments of the invention is performed in real time. Real time in the sense of the invention means that the time elapsing between extension of the nanoscanner and registration of the extension is not larger than 1 s, 0.1 s, 10 μs or 1 μs. A real time monitoring can enable a real time adjusting of the probe's level, wherein the time elapsing between extension of the piezo element and adjusting the level of the probe is not larger than 1 µs, 10 µs, 100 µs, 1 s or 5 s.

According to one embodiment, adjusting the level of the probe according to the above aspect and embodiments of the invention is performed by lowering or lifting the probe or lowering or lifting the sample.

According to another embodiment, adjusting the level of the probe according to the above aspect and embodiments of the invention is automatically performed. Such automatically adjusting may performed by the actuator described above or a programmed microprocessor that is configured to run the method according to any aspects or embodiments of the invention.

According to another embodiment, such programmed microprocessor is configured to monitor the extension of the piezo element and automatically start the actuator to adjust the level of the probe or the sample, when a defined threshold of extension is reached. The microprocessor is further configured to automatically stop the actuator, when a certain lowering or lifting distance along the first direction is reached.

According to another embodiment, the level of the probe is adjusted, when the nanoscanner exhibits an extension lower than 5, 10, 15, or 20% or higher than 80, 85, 90 or 95% of its maximal extension. Such embodiment offers the advantage to keep the extension of the nanoscanner in the optimal working range between 5, 10, 15 or 20% and 80, 85, 90 or 95% of the maximal extension. At 0% of the maximal extension the nanoscanner is maximally retracted.

Maximal extension in the sense of the invention means the maximal length of a nanoscanner to which the nanoscanner can be extended by application of an electric current. Likewise, minimal extension or maximal retraction in the sense of the invention refers to minimal length of a nanoscanner to which the nanoscanner can be retracted by application of an electric current.

According to another embodiment, the level of the probe is adjusted by lowering or lifting the probe or the sample by 5 to 30% of the maximal extension of the nanoscanner. Such embodiment offers the advantage of restoring the optimal working range of the piezo element.

According to a preferred embodiment, the level of the probe is adjusted by lowering or lifting the probe or the sample by 20% of the maximal extension of the piezo element.

According to another embodiment, the level of the probe is adjusted, when the nanoscanner exhibits an extension that is 50 nm, 100 nm, 200 nm, 500 nm, 700 nm, 1µ, or 2 µm before the maximal extension or that is 50 nm, 100 nm, 200 nm, 500 nm, 700 nm, 1µ, or 2 µm before the maximal retraction. Such embodiment offers the advantage of keeping the extension of the nanoscanner in the optimal working.

According to another embodiment, the level of the probe is adjusted by lowering or lifting the probe or the sample by at least 50 nm.

According to a preferred embodiment, level of the probe is adjusted by lowering or lifting the probe or the sample by 3 µm. Such embodiment offers the advantage of restoring the optimal working range of the piezo element.

Wherever reference is made above to an embodiment of the invention, and such embodiment only refers to one feature of the invention, it is intended that such embodiment may be combined with any other embodiment referring to a different feature. For example, 15 areas of 50 by 50 points may be measured employing a tip of radius 10 nm.

According to another aspect of the invention, a system for classifying a tumour tissue sample is provided, comprising a device for determining stiffness values with a spatial resolution of at least 1 mm, preferably 100 µm, 10 µm or 1 µm, a programmed microprocessor, wherein the programmed microprocessor is equipped and configured to run a method according to the above aspects or embodiments of the invention.

Such device may comprise a stylus, a sample support, and means for registration of the stylus movement, wherein the stylus is movable in a vertical direction (z-axis) and either the stylus or the sample support is movable in a lateral direction (x- or y-axis) or either the stylus or the sample support is moveable in both vertical and lateral directions.

Such stylus may be a cantilever with a tip, wherein the cantilever has a spring constant of 0.01, 0.025, 0.05, 0.06, 0.075, 0.1, 0.15, 0.2, 0.25, 0.3, 0.5, 0.75, 1 or 10 $Nm^{-1}$ and radius of the tip is 0.01, 0.02, 0.05, 0.07, 0.1, 0.5, 1, 1.5, 2, 2.5, 3, 3.5, 4, 4.5 or 5 µm.

Such means for registration of the stylus movement may be optical system comprising a laser and a split diode, wherein the laser is focused on the back of the cantilever and reflected onto the split diode and deflections of the cantilever are registered by a changing position of the reflected laser light on the diode, or an interferometer, wherein interference of two light beams can be used for deflection measurement. Alternatively, the cantilever may comprise a piezoelectric element, wherein a charge is generated by the deflection of the cantilever.

Such programmed microprocessor may be integrated into the device described in the preceding paragraphs or may be part of a control unit or a computer for operating the device.

According to a preferred embodiment, the device for determination of stiffness is an atomic force microscope.

According to a preferred embodiment, the device (100) is an atomic force microscope that comprises a probe (2) having a tip (21) for interacting with a sample (4), wherein said probe (2) is configured to move said tip (21) towards said sample (4) along a first direction (R), and a nanoscanner (1) for retaining said sample (4) or said probe (2). The device (100) comprises a means for monitoring the extension of said piezo element along said first direction (R), an actuator (3) for adjusting a level of said probe (2) along said first direction (R) and a controller (31) for controlling said actuator (3), wherein said controller (31) is configured to control said actuator (3) so as to adjust said level of said probe (2), when said nanoscanner (1) exhibits an extension below or above a threshold value.

Such actuator is configured to lower or lift the sample or the probe to prevent the probe's tip from coming to close to the sample or from being to far way from the sample.

Such means for monitoring the extension of the nanoscanner may be may be optical system comprising a laser or an interferometer, a piezo electric sensor, which can register the movement of the piezo element as an electrical charge, or a sensor which is monitoring not only applied voltage but also the consequent real extension in order to ensure high precision of the extension.

Alternatively, such means for monitoring the movement may be the reading of the voltage or the electric current applied to the nanoscanner, which is necessary to move the nanoscanner along the first direction or, in particular, to maintain a constant force between tip and sample. For example, each piezo has specific sensitivity—nm/V which is used to convert applied voltage to the piezo distance/movement When the applied voltage or electric current and resulting nanoscanner extension reach a specific level then the adjusting the level of the probe as described above is activated.

A controller in the sense of the invention refers to a control unit that is connected to the actuator. Such controller may a microprocessor or a computer.

The nanoscanner may be directly coupled to the probe or the sample. In case of the probe is part of a probe assembly, the nanoscanner alternatively may be directly coupled to the probe assembly.

According to one embodiment of the above aspect of the invention, the nanoscanner is configured to maintain a constant probe tip-sample interaction force. Such force has been described above.

According to another embodiment of the above aspect of the invention, the nanoscanner is configured to maintain a constant indentation depth of the probe tip into the sample.

According to one embodiment of the invention, the nanoscanner is a piezo element. The term piezo element has the same meaning as described above.

According to one aspect of the invention, the probe is a cantilever. The term cantilever has the same meaning as described above.

According to one embodiment of the above aspect of the invention, the nanoscanner is movable in a second direction which extends orthogonal to the said first direction described above.

According to one embodiment of the above aspect of the invention, the device further comprises a sample holder for retaining the sample. The term sample holder has the same means as described above. In case of the sample is retained by the sample holder, the nanoscanner may be directly coupled to the sample holder.

The invention is further characterized by the following figures and examples, from which further features, advantages and embodiments of the invention can be derived:

EXAMPLES

Materials and Methods

Mammary and Lung Tissue Samples from MMTV-PyMT Mice

To obtain female mice heterozygous for the PyMT transgene, male PyMT mice on a C3H/B6×FVB-C3H/B6 background were randomly bred with C3H/B6 females lacking the PyMT transgene. Mice were palpated twice weekly to assess mammary tumour onset. Tumour volume was calculated following caliper measurement as width×length×0.4. Mice were euthanized by $CO_2$ inhalation.

MMTV-PyMT transgenic mice exhibit multiple tumour sites and several glands were removed. They were immediately placed in ice-cold sterile Ringer's solution (6.00 g NaCl, 0.40 g KCl, 50 g anhydric glucose, 0.27 g CaCl2, 3.20 g lactic acid in a 1000 ml of an injectable water) supplemented with a protease inhibitor cocktail (Complete). For nanomechanical AFM testing, cylindrical specimens that represent a cross-section of the entire tumour were obtained by a biopsy punch with an inside diameter of 2 mm. Stiffness mapping was started within 1 h after biopsy and continued for up to two days. The mechanical properties of mammary tissue samples remained unchanged during this time period.

Measuring Hypoxia In Situ

Tumour bearing mice were injected intraperitoneally with pimonidazole hydrochloride at 100 mg/ml in 0.9% sterile saline solution (120 mg/kg, hypoxyprobe-1, HPI). After 90 minutes mice were sacrificed and biopsies taken for nanomechanical testing as described above. Subsequently, hypoxia was assessed by immunohistochemical analysis of pimonidazole incorporation.

Human Biopsies

Human biopsies were obtained from the Breast Treatment Center of the Basel University Women's Hospital directly after removal. Patient recruitment and stiffness analysis was carried out in accordance with ethical requirements and without previous knowledge of clinical data. The ultrasound-guided core biopsy of the conspicuous lesion removed an approximately 2 mm-diameter radial, cylindrical specimens between 0.2 and 1 cm long that was directly transferred to a vial containing ice-cold sterile Ringer's solution supplemented with glucose and a protease inhibitor cocktail (Complete). As for murine tissues, AFM testing started within 1 h after biopsy. Mechanical properties of specimens did not change during this time period. The specimens were kept at 4° C. until AFM measurements to minimize tissue degradation. AFM analysis was performed no later than three days after removal to avoid autolytic effects (i.e., tissue self-degradation) on the specimen.

Nanomechanical AFM Testing

Figure 1:
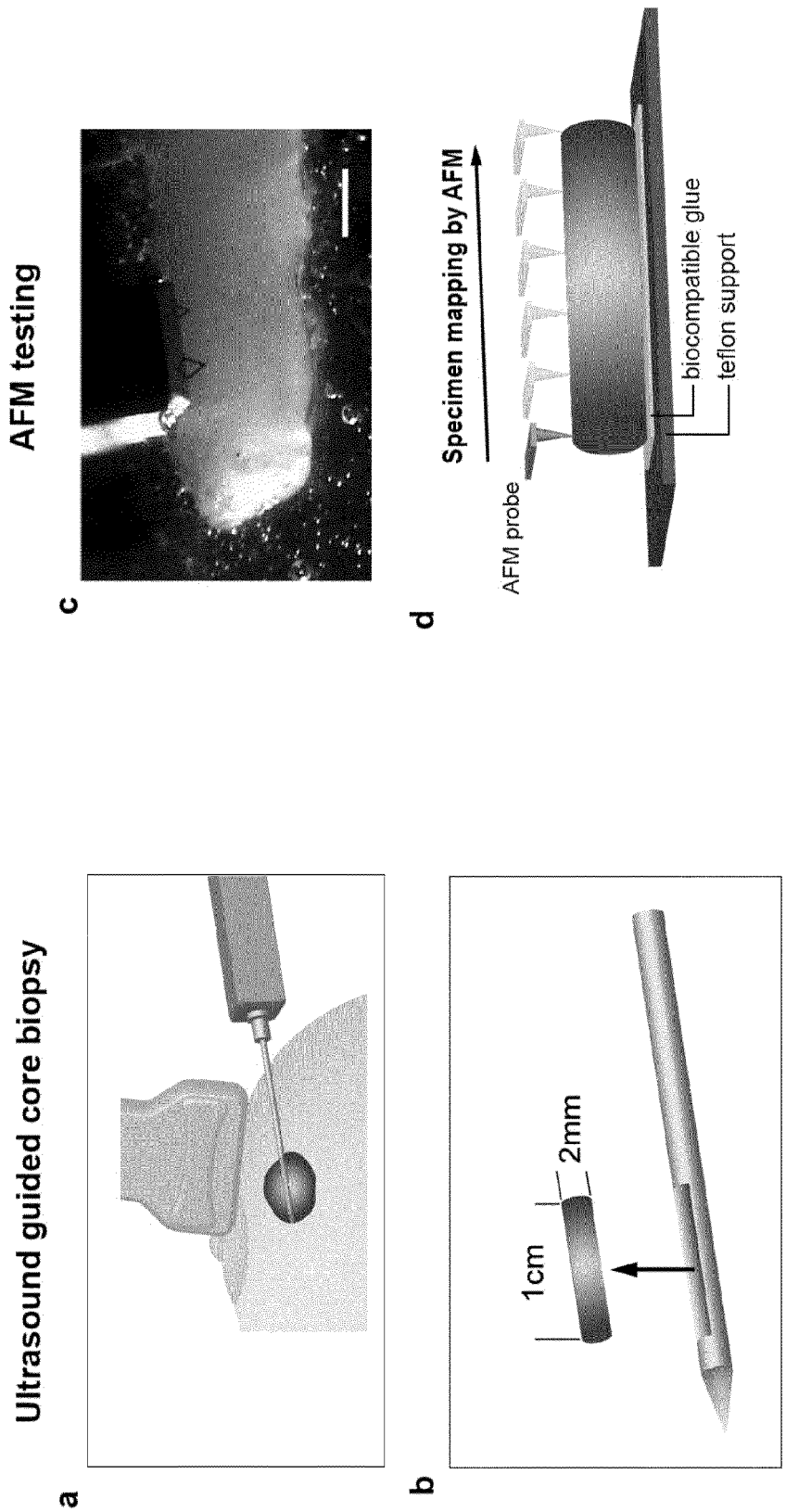
FIG. 1 shows a schematic representation of experimental approach in nanomechanical AFM testing biopsies (scale bar=500 μm).

Automated leveling was regulated by a custom set of algorithms during data acquisition to correct for the natural unevenness of tissue. Each sample was examined in a systematic manner from one edge to the other to account for possible heterogeneities. A regular distance of approximately 500 µm was kept between the scan regions where the distance between the two cantilevers served as a reference (FIG. 1). This resulted in roughly 10 to 15 FV maps per specimen depending on the total biopsy length. Given that obtained specimens from mouse mammary glands and lungs were not cylindrical as human biopsies, scanning areas were chosen so as to assure that the specimens were covered throughout.

For the analysis of the mammary gland tissue samples by AFM, biopsies were glued onto a round Teflon disk using 2-component glue or fixed to a Petri dish with 5-minute fast drying epoxy glue. After a pre-drying step of 2 minutes (to avoid mixing of the epoxy and the specimen buffer), the specimen was laid flat in order to optimize the indentation angle and to avoid influence from external components (e.g. the cantilever holder). Pipette tips acting as "ramps" were placed directly under uneven segments of each specimen to maintain height consistency. The use of excessive force (e.g. tearing or stretching) was minimized at all times during specimen handling. All preparative steps were performed in a sterile buffer environment supplemented with protease inhibitors to prevent contamination and to ensuring that the specimen remained in a close-to-native state. The mounted specimens were kept in ice-cold Ringer's solution until nanomechanical testing, which was performed at room temperature or at 37° C.

For sharp pyramidal tips (200-mm-long silicon nitride cantilevers, nominal cantilever spring constant $k=0.06$ $Nm^{-1}$, resonance frequency [air]=18 kHz). The exact spring constant k of the cantilever was determined prior to every experiment with the thermal tune method while the deflection sensitivity was determined in fluid using solid glass substrates as an infinitely stiff reference material.

Stiffness (elastic modulus, E) measurements of biopsies were derived as follows; load-displacement curves, also designated as force indentation curves, were recorded at a given site in an oriented manner during both loading and unloading. A regular distance of approximately 500 µm was kept between the scan regions where the distance between the two cantilevers served as a reference. An individual set of data consisted of 1,024 load-displacement curves, at a sampling rate of 1.5 Hz. This resulted in roughly 15 to 20 force volume maps per sample. When possible, force-volume maps (FV) were made over a 24×24 point grid with a scan size of 20×20 µm at a rate of approx. 0.8 load/unload cycles per second. Each load-displacement curve consisted of 512 data points whereas the Z length was set to 5 µm to 8 µm depending on the properties of the analyzed region. Each FV map was set to 20×20 $\mu m^2$ in order to (i) optimize experimental time as well as (ii) to provide a sufficiently large area incorporating all components within the tissue (e.g., cells and extracellular matrix). The maximum applied loading force was set to 1.8 nN and an indentation depth of approximately 150 to 3000. Additional 72×72 FV maps (5184 force-displacement curves per map and a pixel size of 277 nm) were obtained to increase the spatial resolution over key areas of interest.

AFM Data Analysis

Force indentation curves were analyzed using a method described previously (Oparic, et al., *Biophysical Journal*, 98(11): p. 2731-40, 2010, Plodinec, et al., *Journal of Structural Biology*, 174(3): p. 476-484, 2011). Briefly, software was developed in LABVIEW for the automated analysis of the FV data. The contact point was determined by applying a polynomial fit to raw force curves based on a published algorithm (Lin, et al. *Journal of Biomechanical Engineering-Transactions of the Asme*, 129(6): p. 904-912, 2007). Force curves were obtained by the indentation h, which corresponds to the difference between piezo displacement and cantilever deflection, and by multiplying cantilever deflection d with the spring constant k to obtain the load F. Unloading force curves were analyzed by performing a linear fit to the upper 50% of the force curve, which defines the stiffness between the maximum load F=1.8 nN and the minimum load of 0.9 nN. Extraneous effects on the force curve such as adhesion could be avoided by this procedure. The Poisson ratio was set to 0.5. The Young's modulus was determined according to the Oliver and Pharr method (Oliver et al., *Journal of Materials Research*, 7(6), 1564-1583, 1992). The slope values were spatially plotted to yield color-coded stiffness maps in Igor Pro 6.22. A 2D second degree spline interpolation was performed on the 2D stiffness maps to smoothen the visual presentation of the data.

Immunohistochemical Analysis

After AFM, all samples were retrieved, formalin-fixed and paraffin-embedded according to standard histological procedures. Sections of approx. 5 µm thickness were cut and transferred onto glass slides. The first and the last slide of sequential sections were routinely stained with Haematoxylin & Eosin (H & E). Subsequent histopathological examination included assessing the type of lesion (invasive ductal carcinoma, DCIS, fibroadenoma etc.) and a number of standard histopathological markers (extent of tumor infiltration, fibrosis, necrosis, and lymphocytic infiltration). For immunohistochemical analysis (IHC) of the remaining slides of human mammary tissues, the following antibodies were used: anti collagen I (1:80; Biologo CO2111, USA), anti laminin (1:25; Thermo RB-082-A, Thermo Scientific, USA), anti vimentin (prediluted, Ventana 790-2917, Roche Diagnostics, CH), anti desmin (prediluted, Ventana 760-2513, Roche Diagnostics, CH). IHC analysis of murine tissue sections for laminin, desmin and vimentin was performed in the same manner as for human sections. In addition, murine sections were stained with anti β1 integrin (1:50, Abcam, ab52971, USA) and anti-mouse collagen I (1:800, Abcam, ab34710, USA). In some cases, sections were treated for antigen retrieval by heat, or with 10 mM Tris buffer, 1 mM EDTA, pH 9.0 and Citrate buffer, pH 6.0. For collagen staining of human biopsies, sections were pre-treated with pepsin for 30 minutes at room temperature. Avidin/biotin was used for blocking the nonspecific binding of the primary antibody. For immunolabeling, sections were incubated with 100 µl antibodies correspondingly diluted in 10 mM PBS, pH 7.6 and 0.1% sodium azide. Staining was visualized with horseradish peroxidase (HRP)-conjugated secondary antibodies (DakoCytomation, Denmark). Sections were examined with an upright light microscope (Carl Zeiss, Germany) at the magnifications indicated.

Statistical Analysis 21 human biopsies from 20 different patients were analyzed in the present invention (see Table 1). In addition, 32 mammary glands and 6 lungs obtained from 16 MMTV- PyMT mice were analyzed. Out of the 6 lungs, three were healthy and three exhibited metastatic lesions. All individual stiffness values were summarized in OriginPro 8.5 to obtain stiffness distributions for each specimen (henceforth defined as global histogram). The bin width was set to 200 Pa for all mammary gland specimens and 500 Pa for the murine lungs. Counts were normalized according to the total amount of data points per specimen. Data fitting was performed by first locating distribution peaks using the OriginPro peak analysis application and subsequently applying multi-peak fit to the stiffness distributions.

All data are given as mean±standard deviation (s.d.). Statistical significance of differences in mean values was assessed with the paired Student's t test—in Origin 7.5. Statistical significance was set at $P \leq 0.05$.

Example 1

Nanomechanical Testing of Soft Tissue Biopsies by AFM

Figure 2:
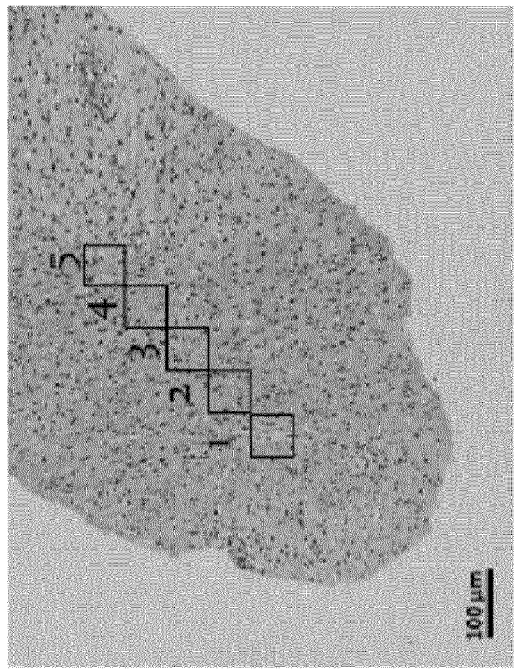
FIG. 2 shows a human breast biopsy fixed to a petri dish and a histological assessment of the biopsy.
Figure 2:

Nanomechanical properties of soft breast tissue biopsies from MMTV-PyMT transgenic mouse and from human patients were assessed under physiological buffer conditions by AFM. The sample used for AFM testing was excised from the mammary gland in shape of a radial, cylindrical biopsy (FIG. 1a). A typical cylindrical tissue sample exhibits a distinct orientation from core to the periphery. Fresh tissue samples are stably attached to a solid Teflon support with biocompatible glue an oriented manner as shown in FIG. 1d. In these samples, 3D tissue integrity and heterogeneity is preserved and the corresponding structural and nanomechanical information throughout the entire specimen is presented in a 2D plain to the AFM probe (FIG. 2). This allowed the measurement of the nanomechanical response in an oriented manner. Samples were kept in Ringer's solution at all times.

A human breast biopsy was fixed to a petri dish along with the cantilever overlaying the intended scan region (FIG. 2a). The second cantilever serves as a reference to keep a constant distance of 500 μm between the scan regions. The histopathological assessment of the biopsy after AFM testing combined with the previously acquired images can be used to assess the approximate regions analyzed by AFM (FIG. 2b).

Example 2

The Nanomechanical Signature of Human Breast Biopsies

Figure 3:
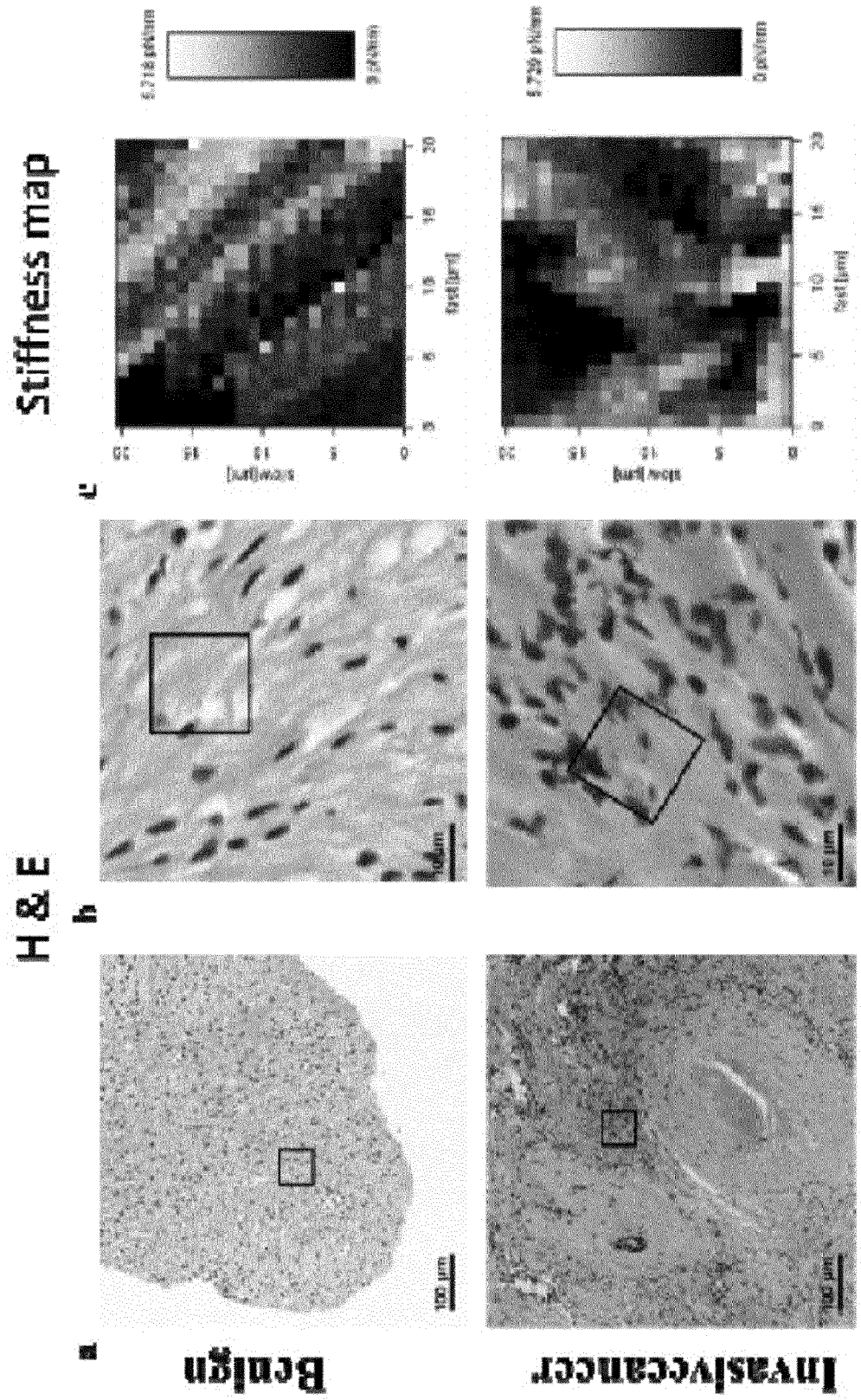
FIG. 3 shows the structural properties of benign lesions compared to invasive cancer assessed by histopathological analysis of the sample after AFM measurements and AFM stiffness determination of the sample.

AFM stiffness measurements of fresh human breast biopsies were carried out to elucidate the diagnostic and prognostic potential of the nanomechanical tissue properties in human breast cancer (FIG. 3).

Histopathological analysis of the samples after AFM measurements reveals the benign or malignant tissue phenotype (FIG. 3a). The data shown in the top panel were acquired from a 34-year old female patient diagnosed with fibroadenoma. The lower panel data originate from a 69-year-old female patient with invasive ductal carcinoma. Benign lesions reveal a strong uniform distribution of fibrous tissue, whereas invasive cancer appears disorganized containing mixtures of tumour cells and fibrotic tumour stroma. These properties are more visible under higher magnification (FIG. 3b) and correlate well with stiffness maps (FIG. 3c) acquired by AFM in the regions denoted by black squares in (FIG. 3b).

Figure 4:
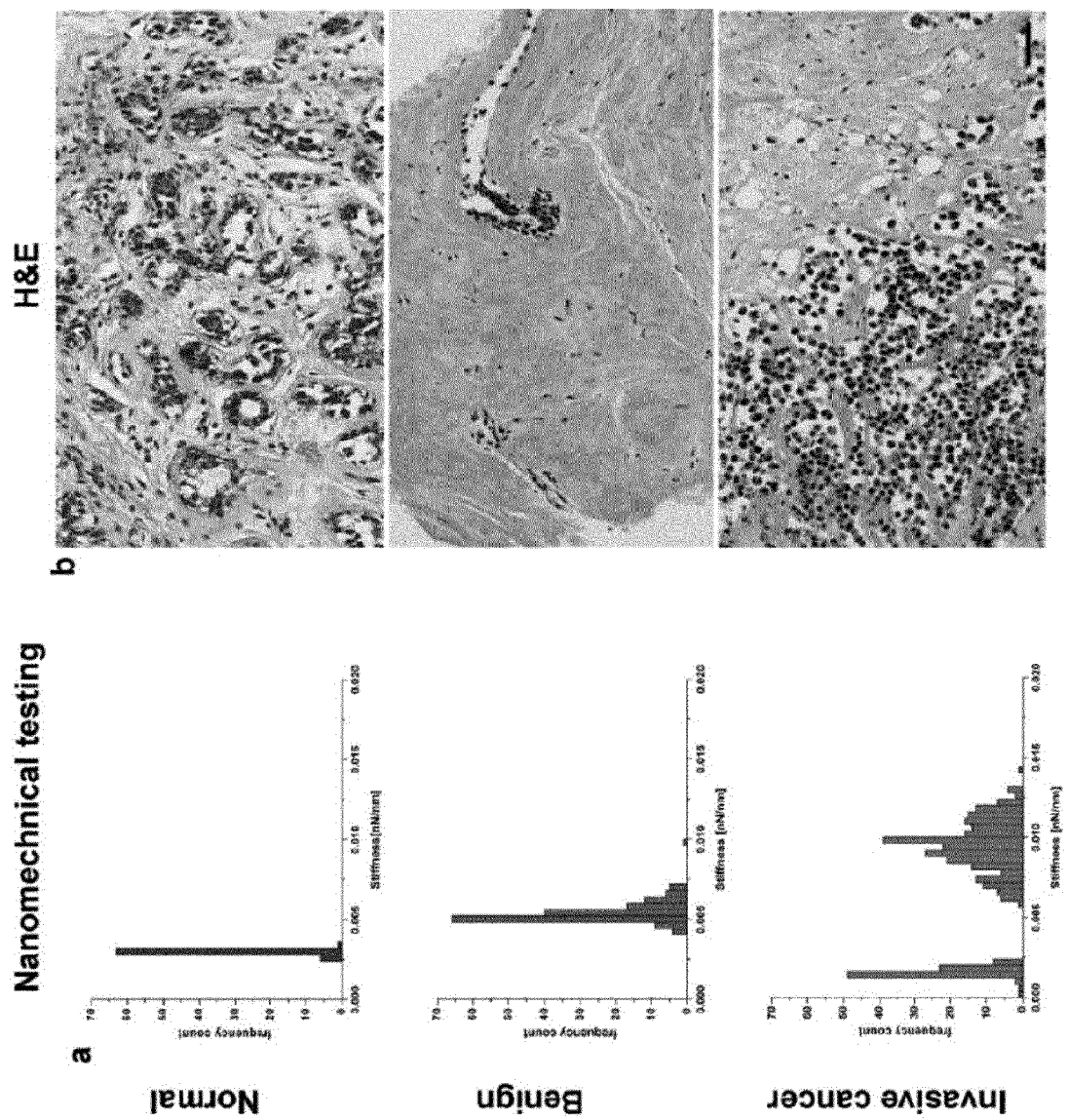
FIG. 4 shows the nanomechanical signature (stiffness distributions) and histopathological assessment of human breast tissue (scale bar=100 μm).

Normal mammary gland tissue (n=4) exhibits a narrow range of stiffness values with a peak of $E$ 1.83±0.69 kPa (FIG. 4a, top panel). H&E staining of a section from the same sample revealed the typical histology of healthy mammary gland tissue from a young female. In the lobular structure, the acini consist of uniform epithelial cells that are separated by a small amount of connective tissue (FIG. 4b). The narrow stiffness distribution measured by AFM correlates well with the homogeneous histomorphological appearance. However, because of the young age and premenopausal state of the patient, it is possible that this particular nanomechanical signature is not characteristic for all normal mammary gland tissues. A rather narrow range of stiffness was also found in samples that proved to be benign lesions, although the $E=4.07\pm1.39$ kPa indicates an increase in stiffness in the 20 samples tested compared to the normal mammary gland. Consistent with this nanomechanical signature, histological examination of the benign lesion from a 60-year old patient demonstrates fairly uniform, predominantly fibrotic tissue with sporadic lobules typical for fibroadenoma (FIG. 4a, middle panel). Benign tumour exhibits mostly uniform proliferation of fibrous tissue typical for fibroadenomas (FIG. 4b, middle panel).

A number of human biopsies (n=12) probed by AFM shows a significantly broader range of stiffness values with two distinct peaks as shown in the bottom panel of FIG. 4a. Histological examination of this biopsy after AFM measurement confirmed an invasive ductal carcinoma, which represents the most common type of breast cancer in women, as shown for the 70-year old patient (FIG. 4b, bottom panel). There, the central areas are dominated by tumour cells that infiltrate in a cord-like pattern into the dense fibrotic tissue at the tumour periphery. Invasive ductal breast carcinoma shows infiltrating nests of cancer cells that have evoked a dense fibrous tissue response. By correlating AFM measurements with histology, the cancer cells from the inner regions of the tumour were identified as the main contributors to the soft peak with $E=0.87\pm0.65$ kPa. Areas characterized by increased stiffness with a peak at $E=11.26\pm1.90$ kPa are mainly situated at the tumour periphery and thus correspond to fibrotic stroma.

A slightly broader but unimodal stiffness distribution with a small increase in overall stiffness is typical for benign lesions (FIG. 4a, middle panel). In contrast, cancer tissue exhibits a bimodal stiffness distribution with two peaks representing soft and relatively stiff regions of the tumour (FIG. 4a, bottom panel). FIG. 4b shows the histopathological assessment of tissue samples after AFM testing. Histology reveals the terminal ductal lobular unit of a normal mammary gland fenced by interstitial fibrous connective tissue and more distant adipose tissue (FIG. 4b, top panel).

Figure 5:
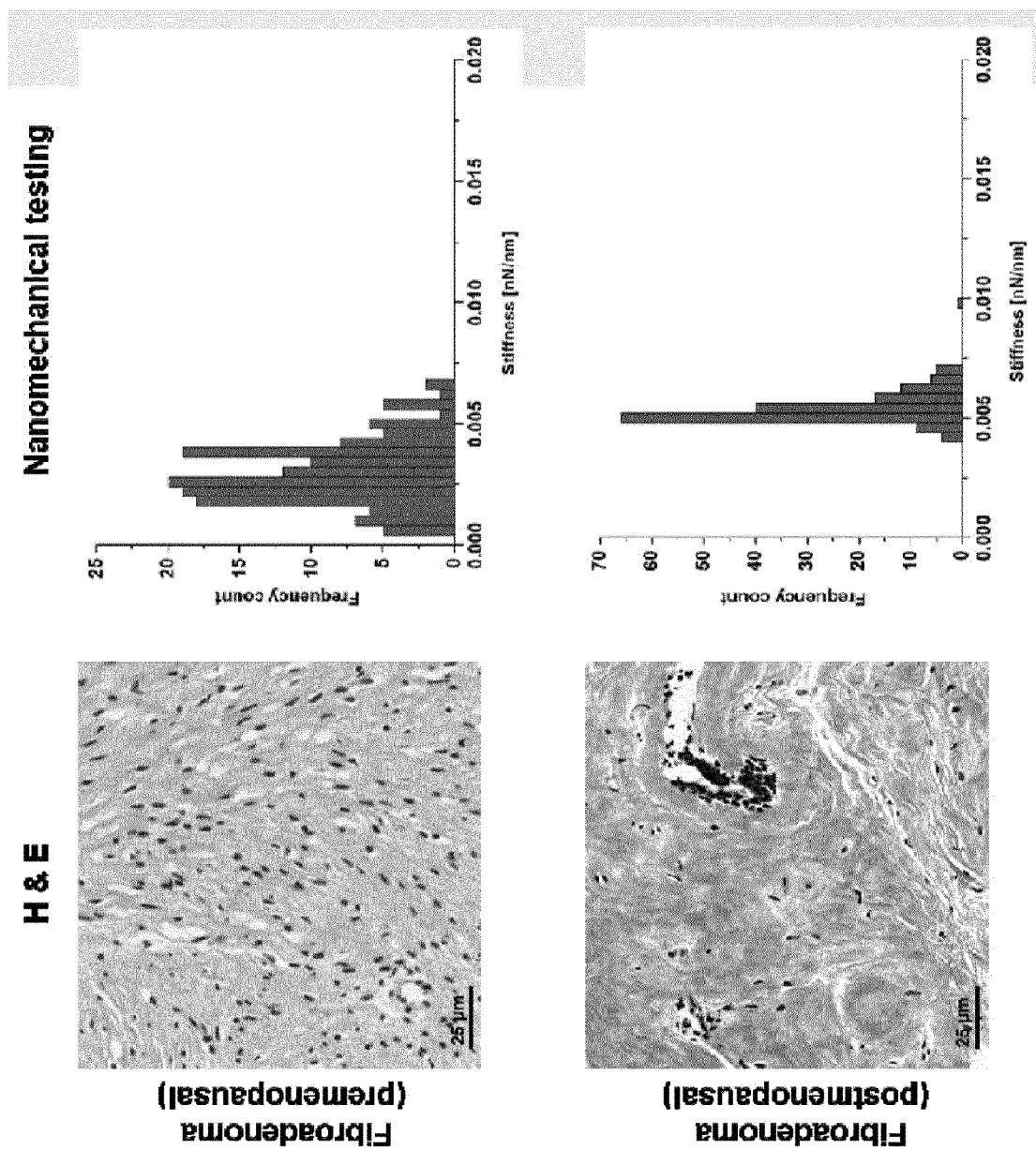
FIG. 5 shows the histological and nanomechanical differences between biopsies from premenopausal and postmenopausal patients assessed with histopathological analysis and stiffness distributions of breast tissue samples.

Histopathological analysis reveals numerous cells still present in the sample obtained from a 34-year old premenopausal patient, whereas the sample obtained from a postmenopausal 69-year old patient exhibits mostly dense fibrous tissue (FIG. 5, left panels). A unimodal stiffness distribution can be observed in both stiffness measurements (FIG. 5, right panels), yet the stiffness values and the distribution width vary notably.

The shift to the softer peak measured for the premenopausal patient correlates well with the increased cell density in the premenopausal sample (FIG. 5). Importantly, the data obtained on human breast biopsies provide evidence that the nanomechanical properties of tissue biopsies can be used as a reliable marker to detect malignant transformation and tumour progression in human patients.

Example 3

Figure 6:
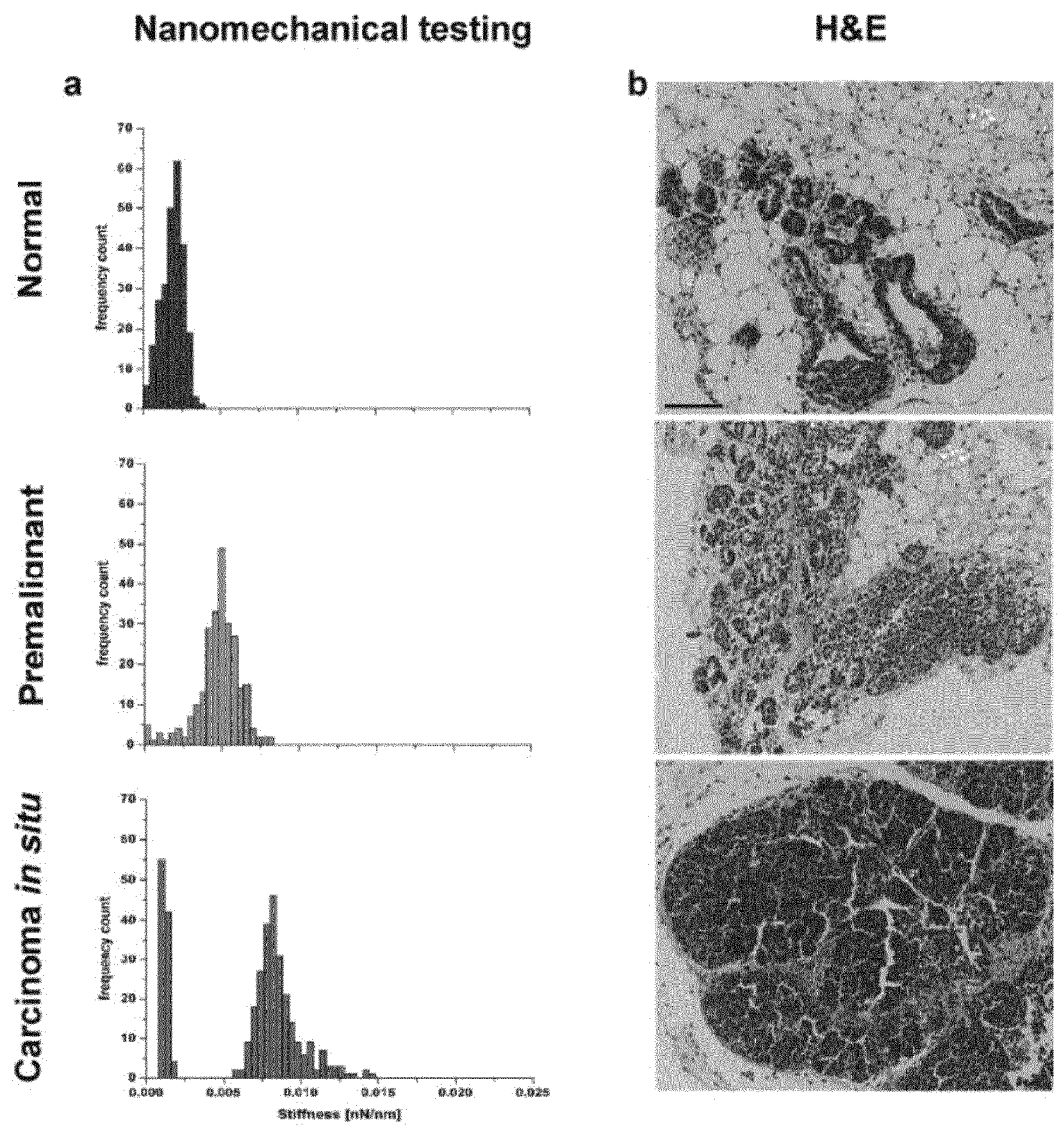
FIG. 6 shows the correlation of the nanomechanical response with histology in MMTV-PyMT mouse mammary gland tissues (scale bars=50 μm) with stiffness distributions and histological analysis.

Correlating Histopathological Findings with the Nanomechanical Response in the MMTV-PyMT Mouse Model Tissue samples from mammary glands of MMTV-PyMT transgenic mice were removed at different tumour stages to assess the nanomechanical changes associated with tumour progression. Histograms showing the frequency distribution of stiffness values from AFM measurements are depicted in FIG. 6a. AFM measurements of normal mouse mammary gland (n=3) revealed a homogeneous (uniform Gaussian) distribution of stiffness with an elastic modulus E=1.28±0.12 kPa (FIG. 6a, top panel). Correlative histology examination of the specimen confirmed a normal, healthy mammary gland tissue appearance with high amounts of fat tissue that most likely contributes to the low stiffness values (FIG. 6b, top panel). In the premalignant lesions (n=3), the stiffness distribution is broader but still remains unimodal Gaussian (FIG. 6a, middle panel) but stiffness increases to E=4.38±0.55 kPa. Histology revealed a densely packed, hyper-proliferating breast epithelium that correlates well with increased tissue stiffness (FIG. 6b, middle panel). However, the uniform stiffness distribution is lost in cancerous lesions (n=8), and instead, carcinomas in situ exhibit a bimodal stiffness distribution (FIG. 6a, bottom panel) indicative of two distinct mechanical phenotypes. In these early stages of tumour development, the E=0.54±0.13 kPa of core regions is 8-fold lower than that of benign lesions and 3-fold lower than normal tissue stiffness. The soft core is surrounded by significantly stiffer areas of E=16.97±6.89 kPa. Although the bimodal stiffness distribution of carcinoma in situ suggests two distinct populations of cells in the tumour, the histological appearance of the tissue section does not reveal any significant morphological differences among the cancer cells that could contribute to bimodal stiffness distribution (FIG. 6 b, bottom panel). In the carcinoma in situ, the loss of tissue organization and the presence of cancer cells within individual ducts are clearly visible. However, cancer cells look cytologically similar. It is noteworthy that in carcinoma in situ, the surrounding stroma appears unaltered compared to myoepithelium.

In conclusion, correlative comparison of AFM stiffness measurements with histology allowed establishing an association between the nanomechanical response of mouse mammary tissues and malignant transformation; tissue morphology did not provide an apparent explanation for the bimodal stiffness distribution and the soft core region of primary cancerous lesions.

Example 4

Hypoxia-Induced Tissue Softening in Breast Cancer of -MMTV-PyMT

Tumour hypoxia caused by inefficient vascularization has been described for a wide range of solid tumours. It is associated with poor prognosis following radiation, chemotherapy and surgery. Interest in the hypoxic status of tumours has further increased with the discovery that hypoxia regulates dozens of genes that alter cellular behavior and result in a more malignant tumour phenotype. Because a hypoxic core is known as to be a crucial feature of aggressive cancer progression, it was examined whether the bimodal stiffness distribution observed from the periphery to the core of the primary cancer lesion is related to reduced oxygenation. To directly correlate hypoxia and tissue stiffness in staged tumour samples, MMTVPyMT mice were injected with pimonidazole agent that selectively binds to oxygen-starved cells prior to tumour excision. Subsequently, the nanomechanical properties of the tissue samples were tested by AFM and tissues were later processed for hypoxia assessment. Immunohistochemical staining revealed that normal glands and benign lesions are negative for hypoxia, whereas primary tumours exhibit clear hypoxia in the core, that correlates well with the significant decrease of stiffness.

Figure 7:
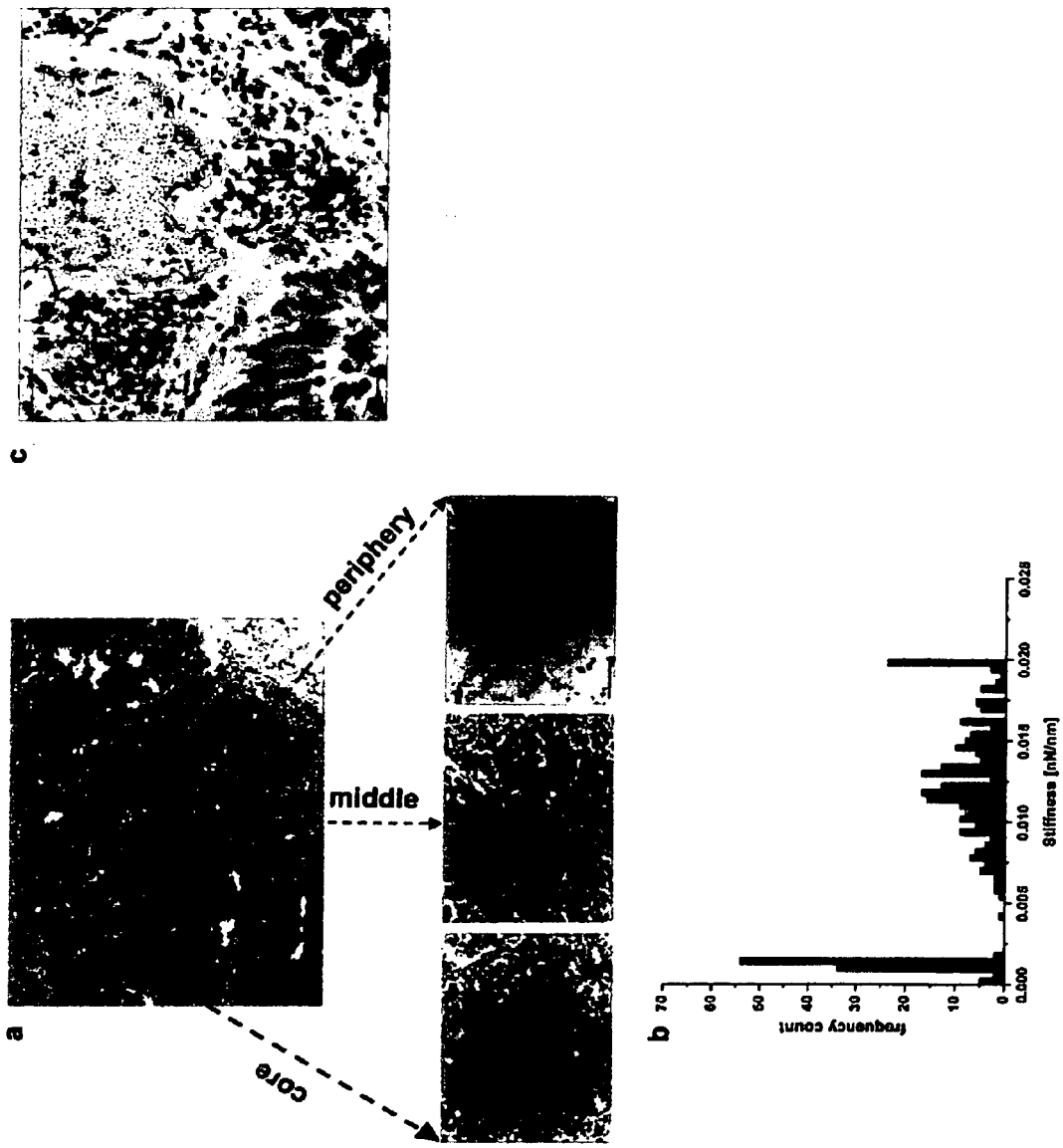
FIG. 7 shows the hypoxia-related stiffness heterogeneity in invasive breast cancer of MMTV-PyMT mice (scale bar=50 μm) in immunolabelled tissue sections and in a stiffness distribution of the tissue samples.

Upon progression of malignancy to the invasive metastatic stage (FIG. 7), a pronounced spread of hypoxia occurred. In addition to the extensive hypoxia in the core (FIG. 7a, zoom in, right panel), this stage is characterized by a progressive dissemination of hypoxic cancer cells (stained dark grey) to the surrounding tissue. In particular, blood vessels were lined with hypoxic cells (FIG. 7a, zoom in, middle panel) suggesting intravasation and ultimately invasion at distant sites and hypoxic cells spread to the peripheral tumour stroma (FIG. 7a, zoom in, right panel). Corresponding AFM measurements show that invasive carcinomas no longer exhibit two distinct stiffness peaks but rather a broad stiffness distribution with gradual stiffening from the core to the tumour periphery. The softness of the core region and the general broadening of the stiffness distribution (FIG. 7b) are consistent with immunohistochemical hypoxia assessment, which shows hypoxic cells disseminated from the core to/and at the periphery. This finding suggests that hypoxia is indeed associated with an invasive, more aggressive cancer phenotype.

At low magnification, the immunolabelled tissue section of invasive breast cancer from pimonidazole-treated mice shows different hypoxic areas (FIG. 7a, dark grey signal). Zooming-in reveals a more detailed view. Hypoxic cells are abundant in the core region of the tumour (left panel), are streaming towards tumour blood vessels (middle panel), and have disseminated to the tumour periphery (right panel, marked by dashed lines). Scale bars are 200 μm and 50 μm, respectively. A histogram displaying stiffness measurements exhibits a bimodal distribution (FIG. 7b). There is an increase in stiffness from the core to the periphery where the stiffness values are broadly distributed.

AFM stiffness measurements indicate that mechanical aspects are valuable markers for cancer progression. Based on the corresponding hypoxia assessment we conclude that tumour

Example 5

Additional Nanomechanical Testing of Human Breast Biopsies

Figure 8:
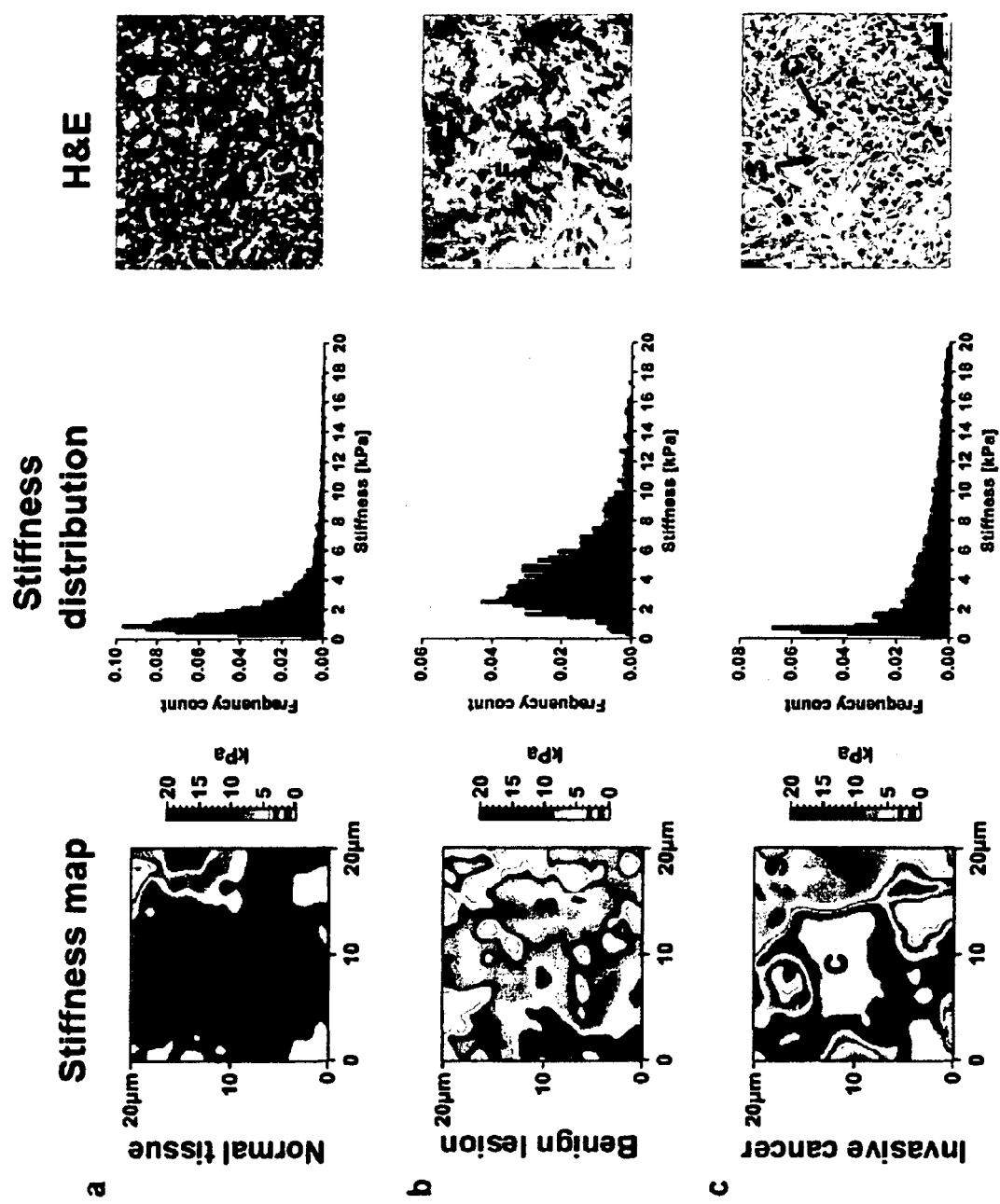
FIG. 8 shows the nanomechanical signature of human breast tissue with representative high resolution stiffness maps, stiffness distributions and histological assessments of normal mammary gland tissue (a), fibroadenoma (begin) lesion (b) and invasive breast cancer (c) (scale bar=200 μm).

AFM was used to examine ex vivo breast tissues under physiological buffer conditions (FIG. 8). In particular, the respective nanomechanical profiles to pathohistological findings were elucidated and correlated in normal, benign and malignant biopsies (FIG. 8). FIG. 8a shows a representative FV map of normal mammary gland tissue. Plotting the global histogram of the entire specimen reveals unimodal stiffness distribution of 1.13±0.78 kPa (FIG. 8a, middle). The histological appearance in H&E-stained sections of the mapped specimen is defined by healthy ducts (FIG. 8a, right) delimited by two layers of epithelial cells, which are distinguishable by their round nuclei and minimally stained cytoplasm.

Benign fibroadenoma lesions show increased stiffness at 3.68±1.92 kPa (FIG. 8b, middle). Softer features (below 2 kPa) within the stiffness map appear to demarcate individual fibroblasts embedded in the fibrotic stroma (FIG. 8b, left). This is validated by histological examination where fibroblasts are the dominant cell-type within the benign lesion (FIG. 8b, right). In comparison, cancer biopsies typically exhibit a bimodal stiffness distribution with two prominent peaks at 0.61±0.21 kPa ("primary") and 1.54±0.30 kPa ("secondary") (FIG. 8c, middle). At values stiffer than 2 kPa distribution broadens, which reflects the marked heterogeneity within across the sample. The representative FV map (FIG. 8c, left) reveals that the dominant, soft peak is typical for a cancer cell surrounded by stiffer stroma. H&E staining confirms the dominance of tumour cells that infiltrate the stroma in a cord-like pattern (FIG. 8c, right).

Representative high-resolution AFM stiffness map (24×24 pixels) shows normal mammary gland tissue (FIG. 8a, left) that exhibits unimodal stiffness distribution (FIG. 8a, middle). Histology reveals the terminal ductal lobular unit (D) of a normal mammary gland fenced by interstitial fibrous connective tissue marked by arrows (right). High-resolution AFM stiffness map of fibroadenoma (benign) lesion reveals fibrotic stroma (S) intermixed with fibroblast cells (F) (FIG. 8b, left). A broader but unimodal stiffness distribution with an increase in stiffness is typical for benign lesions (FIG. 8b, middle). Arrows point extracellular matrix (S) and fibroblasts (F) typically found in fibroadenoma altered tissues (FIG. 8b, right). In contrast, stiffness map of cancer tissue shows cancer cell (C) embedded in an extracellular matrix (ECM) of tumour stroma (S) (FIG. 8c, left). Bimodal stiffness distribution reveals two peaks representing soft cells and relatively stiff peripheral stroma (FIG. 8c, middle). This is consistent with the histopathological assessment of Invasive breast carcinoma. Arrows point to infiltrating nests of cancer cells (C) that have evoked a dense fibrous tissue response (S).

A schematic representation of an ultrasound guided biopsy removal from a patient with a suspicious lesion is show in shown in FIG. 1a. A drawing of a biopsy tool with a specimen displaying dimensions of a typical cylindrical breast biopsy is depicted in FIG. 1b. A representative cylindrical tissue sample exhibiting a distinct orientation from core to the periphery is shown in FIG. 1c. Fresh tissue samples are kept in Ringer's solution at all times and stably attached to a solid Teflon support with biocompatible glue in an oriented manner (FIG. 1d).

Figure 9:
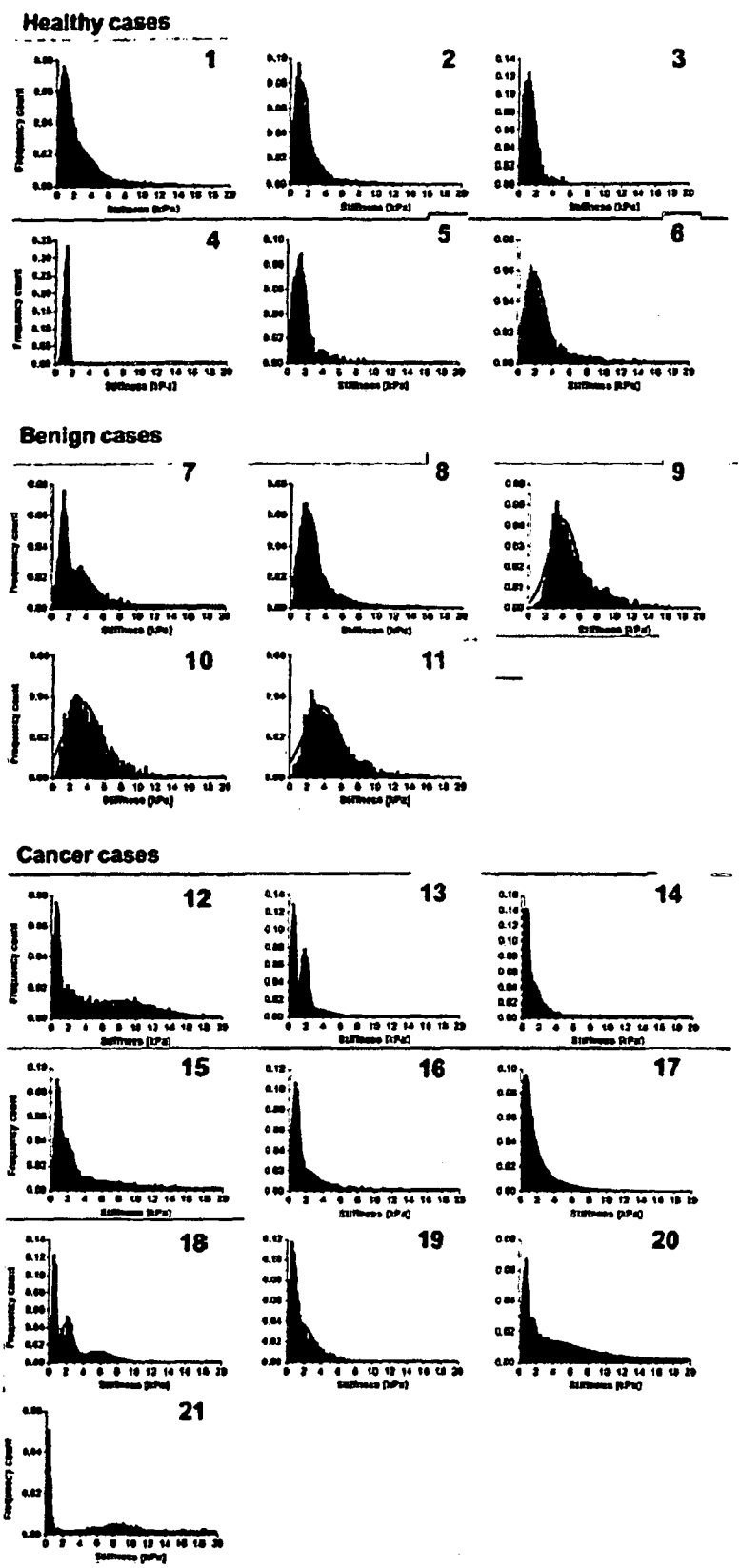
FIG. 9 shows the individual global histograms of the associated Young's moduli for 21 human biopsies incorporated in the present invention.

The global stiffness distributions for all 21 human biopsies (i.e., 6 healthy, 5 benign and 10 cancerous samples) examined are displayed in FIG. 9 (see also Table I). All healthy breast tissues exhibit a unimodal distribution with a characteristic stiffness from 1.13 to 1.83 kPa. A uniform but broader stiffness distribution was found in four cases (cases 8-11) of benign lesions (fibroadenomas). Compared to healthy biopsies, stiffness values ranged from 1.91 and 3.68 kPa and thus indicate a stiffer phenotype in fibroadenomas. In case 8, there was a high abundance of fibroblasts within the mass of fibrotic tissue, which is reflected in the lower stiffness value (1.91±0.99). In one case (7), the global distribution revealed two peaks, one (1.33±0.32 kPa) corresponding to the stiffness value of normal breast tissue, and a second peak at 2.63±2.06 kPa. Consistently, pathohistological diagnosis showed two distinct segments of ductal hyperplasia and fibroadenoma respectively.

Figure 10:
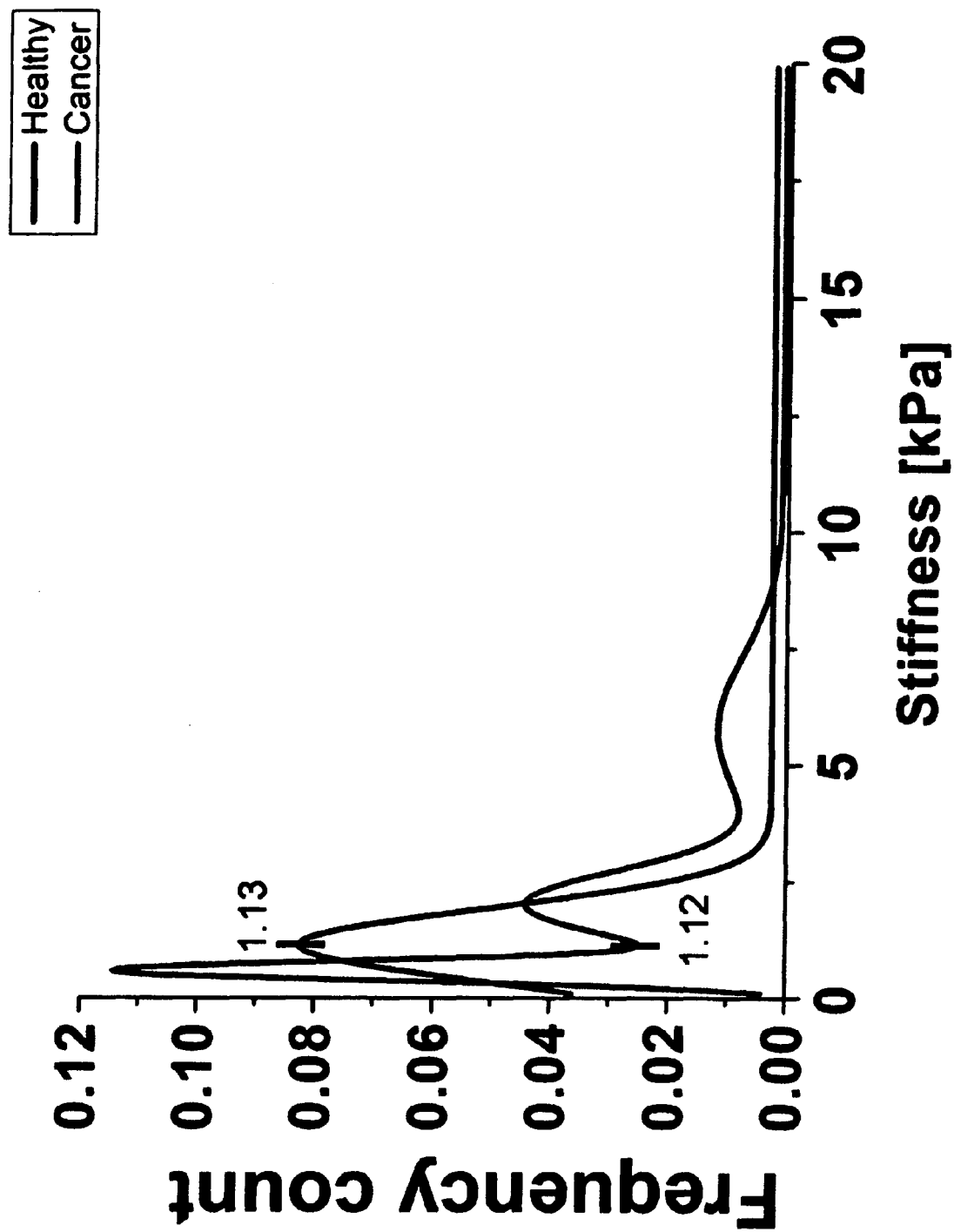
FIG. 10 shows the comparison of two representative global fits from a healthy tissue biopsy and cancer biopsy.

All eleven malignant biopsies shared a stiffness profile with a dominant peak at 0.31 to 0.75 kPa that is significantly softer compared to the stiffness of healthy mammary gland (P<0.0001). Furthermore, the cancer stiffness profile included a second peak between 1.54 and 1.99 kPa that is common to all samples. Another feature typical of malignant biopsies is that the remaining values are broadly spread up to ~20 kPa. This spread is indicative of the overall loss of mammary gland architecture, tumour vascularization and infiltration, and changes of the invasion-afflicted peripheral ECM as a consequence of cancer progression. Interestingly, a distinct minimum (~1.1 to 1.5 kPa) is observed to lie between the primary and secondary peaks in several cancer biopsies. This appears to be inversely correlated to the average stiffness value for healthy tissues (FIG. 10), which arises from the malignant transformation of healthy epithelium. The global distributions from a healthy and a cancer biopsy reveal an inverse stiffness correlation. Healthy tissue exhibits a peak at 1.13±0.78 kPa, whereas within a cancer biopsy a minimum is present in this stiffness range (FIG. 10).

Example 6

Following Nanomechanical Changes Associated with Tumour Progression in MMTV-PyMT Mouse Model for Breast Cancer Because of the genetic and epidemiologic diversity in human patients the MMTV-PyMT mouse model had been chosen to systematically elucidate the nanomechanical footprints of tumour progression and metastasis. According to the pathohistological classification, early hyperplasia in MMTV-PyMT represents normal human mammary glands while extensive epithelial proliferation confined within the basement membrane resembles premalignant neoplasia in humans. Subsequent stages of early carcinoma are morphologically comparable to human ductal carcinoma in situ.

Round cellular structures can be distinguished by an average stiffness of 1.07±0.76 kPa in a representative FV map of normal mouse mammary gland (FIG. 11a, left). In the healthy gland with its well-organized arrangement of densely packed epithelial cells that are delineated by a distinct basement membrane (FIG. 11a, right), the global histogram reveals a unimodal stiffness distribution with a characteristic peak across the entire specimen (FIG. 11a, middle). The uniform stiffness profile found for normal mouse mammary glands is consistent with normal human breast. However, in contrast to human breast tissues, healthy murine mammary glands exhibit excessive amounts of adipose tissue (70-80%) that is characterized by a specific narrow peak with a mean value of 0.31±0.13 kPa (FIG. 19).

Figure 11:
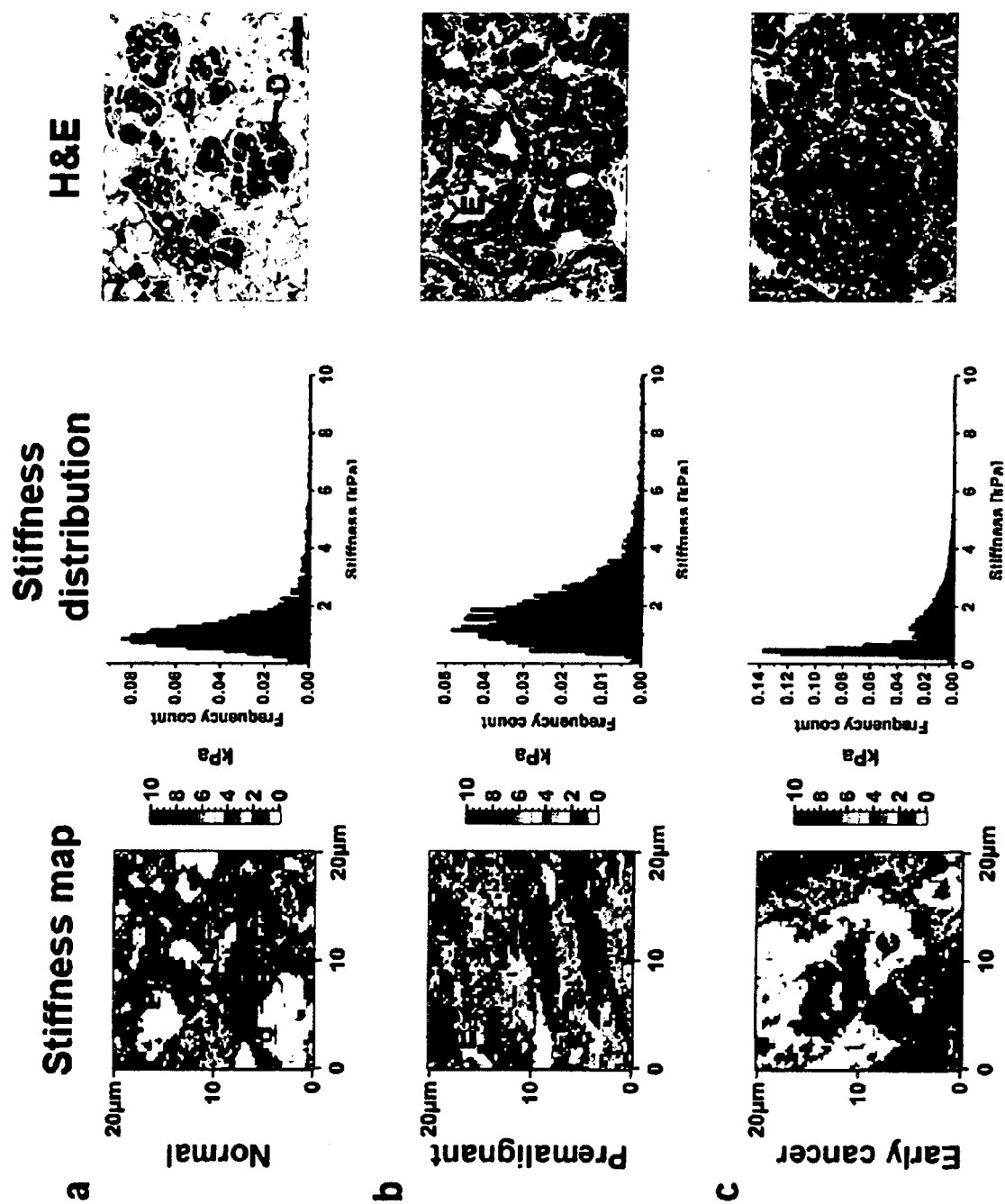
FIG. 11 shows the correlation of nanomechanical response and tumour progression in MMTV-PyMT mice (scale bar=200 μm).

FV maps of premalignant tissues reveal a pattern of soft and moderately stiffer features (FIG. 2b, left) that correlate with an increase of stromal components surrounding the proliferative cell masses in H&E stained sections (FIG. 11 b, right). Accordingly, the global histogram shows a broader distribution with a shift of the peak value to 1.51±0.91 kPa (FIG. 11b, middle). Nonetheless, peak analyzing software was able to two identify two peaks at 1.15 and 1.55 kPa, respectively, indicating the onset of a bimodal stiffness distribution.

Figure 13:
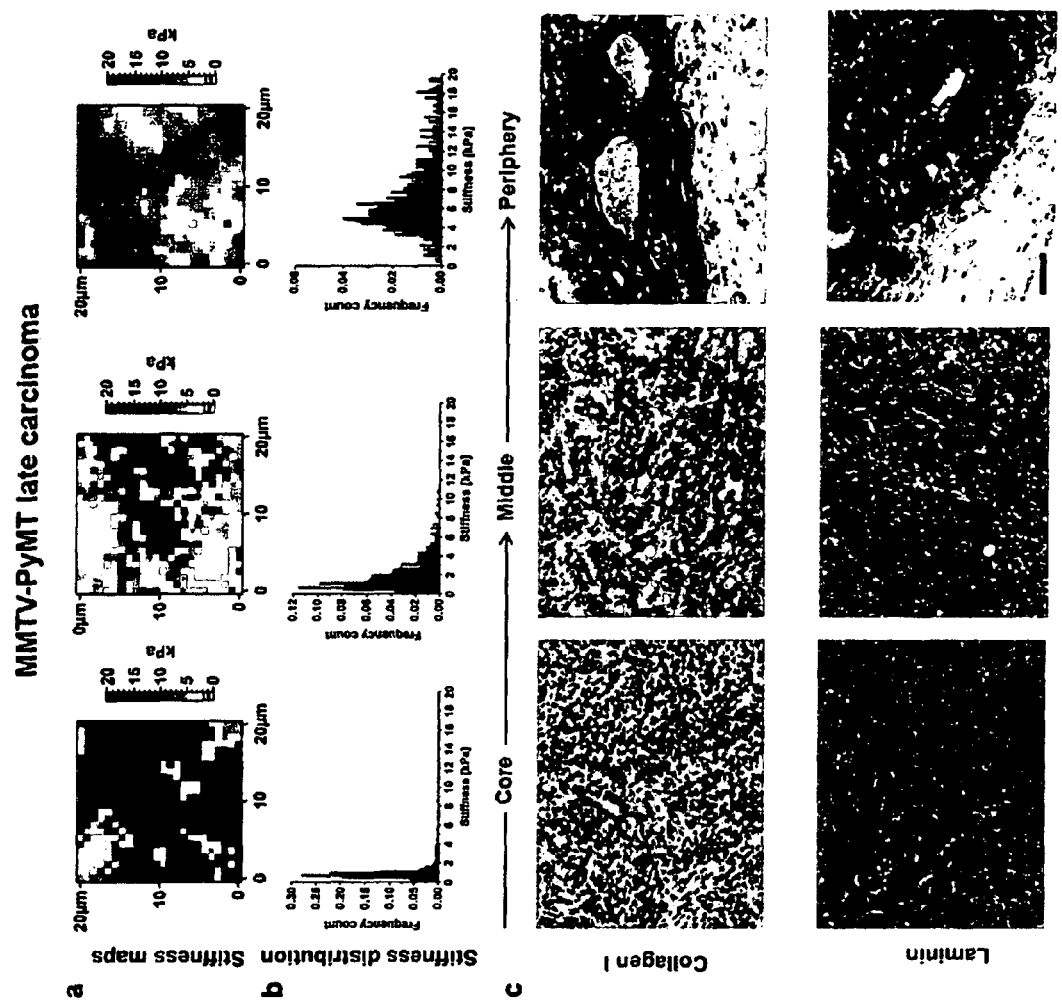
FIG. 13 shows stiffness maps, stiffness distributions and immunohistological assessment of late stage cancer in MMTV-PyMT mice (scale bar=200 μm).

This trend became more pronounced in early cancer resulting in distinct soft and stiff areas (FIG. 13c, left). Peaks at 0.51±0.11 and 1.63±0.71 kPa in the global histogram provide clear evidence of the bimodal stiffness distribution (FIG. 13c, middle). Correspondingly, distinct zones of densely packed cancer cells and early stromal invasion are evident in H&E stained sections (FIG. 13c, right). Stiffness values were calculated for all examined murine mammary tissues and lungs and are displayed in Table 2. In addition, adipose tissue as a major contributor to murine mammary gland composition can be mistaken for cancer cell clusters. Hence, control experiments on adipose tissues were required to discriminate between the two cell types. Generally, adipocytes can be discerned from all other cell types based on their uniform morphological appearance in the H&E-stained sections. Adipocytes lack any distinct structure and are typically larger in size as compared to cancer cells. These features are consistent with what had been observed in the FV maps. The corresponding stiffness value of adipose tissue that was obtained is 0.31±0.13 kPa. In comparison, a representative measurement on cancer cells yielded a primary soft peak at 0.75±0.25 kPa, which is consistent with the analysis from FIG. 8c. Importantly, the data show that adipose tissue is (i) approximately one third softer than malignant cells, (ii) exerts stronger adhesion to the tip (data not shown), and, (iii) exhibits higher dissipative attributes (as characterized by the large hysteresis between approach and retraction AFM force curves) (data not shown).

Representative high-resolution AFM stiffness maps (72× 72 pixels) show ducts for a normal gland (D) (FIG. 11a, left), which exhibits a uniform Gaussian distribution (FIG. 11a, middle). Post AFM histology of mouse tissue sections shows non-lactating mammary gland with a duct (D) surrounded by stromal and adipose tissue (FIG. 11a, right) pointed by arrows. In the premalignant lesion proliferating epithelium (E) and adjacent stroma (S) are visualized (FIG. 11b, left). The stiffness distribution for premalignant hyperplasia (FIG. 11b, middle) is broader with an indication of bimodality (FIG. 11b, middle). H & E sections of the same tissue visualize large proliferation of epithelial cells (E) surrounded by stromal components (S) (FIG. 11b, right). Stiffness map of an early cancer lesion reveals individual cancer cells (C) limited by stromal tissue (S) (FIG. 11c, left). Accordingly, bimodal stiffness distribution discriminates between soft cancer cell phenotype and stiffened stroma (FIG. 11c, middle). In the H & E section arrows point to atypical cell morphology (C) and an early invasion in the adjacent stroma (S) FIG. 11c, right).

Figure 12:
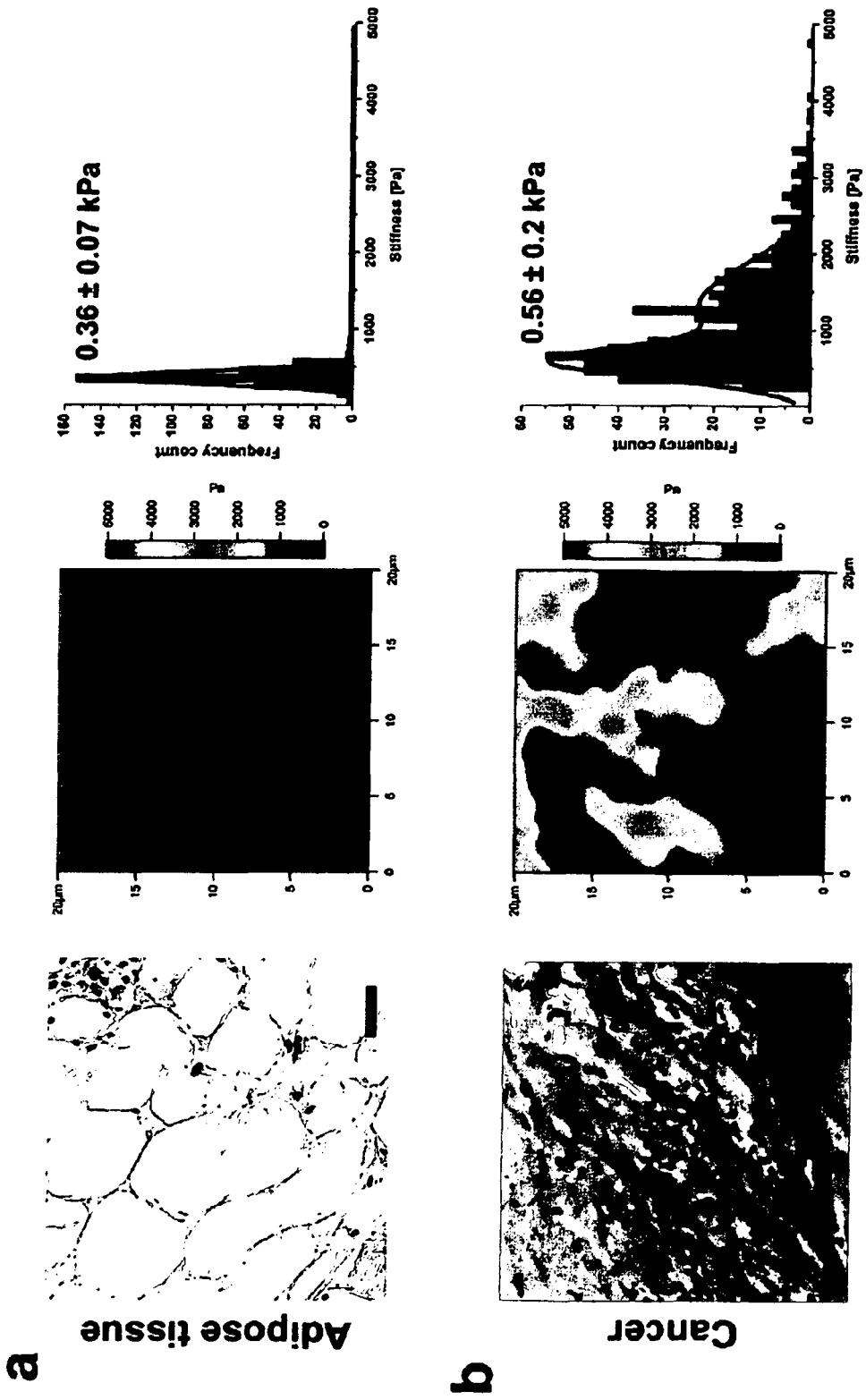
FIG. 12 also shows the structural and nanomechanical markers to distinguish between adipose and cancer affected tissue (scale bar=20 μm).

H&E staining on an adipose tissue of the approximate region is shown in FIG. 12a (left), where the corresponding force maps were recorded. Within force maps, adipocytes appear homogenous (FIG. 12a, middle). Corresponding histogram indicates stiffness distribution and computed mean value for the adipose tissue (FIG. 12a, right). On the other hand, cancer tissue (FIG. 12b, left) exhibits certain structure revealing individual cancer cells embedded in the ECM (FIG. 12b, left and middles respectively). Tissue composed of invasive cancer cells exhibits stiffer and more heterogeneous nanomechanical profile (FIG. 12b, right).

Among the most significant structural changes of mammary gland architecture that occur upon the transition from normal mammary gland to early cancer are the degradation of the basement membrane, which surrounds normal and premalignant glands, and the altered expression and organization of collagen I. In later stages of tumour progression, stromal contributions increasingly modify cancer behavior. For instance, collagen I, the main component of the ECM, has been associated with cancer stiffening. Therefore, the relation was examined between local nanomechanical profiles and ECM structure in late MMTV-PyMT cancer, which corresponds to invasive ductal carcinomas in human. Sequential FV maps demonstrate gradual stiffening from the core to the periphery FIG. 13a) with peak values shifting from 0.74±0.26 kPa in the core to 5.51±1.70 kPa at the periphery. At the same time, tissue heterogeneity increases (FIG. 13b) and is maximal at the periphery (FIG. 13b right). These changes appear to be associated with distinct changes in the ECM as revealed by correlative IHC analysis (FIG. 13c).

Consecutive stiffness maps across the sample demonstrate significant increase in stiffness and structural heterogeneity from core to periphery (FIG. 13a, left to right respectively) as illustrated in corresponding stiffness distributions (FIG. 13b). IHC analysis (dark grey staining) reveals underlying structural and morphological changes in collagen I (FIG. 13c, top) and laminin (FIG. 13c, bottom) from core to periphery pointed by arrowheads.

For example, collagen I is not detected in the soft core, but is increasingly present towards the periphery (FIG. 13c, top). Also laminin I expression is virtually absent from the core (FIG. 13c, bottom left) as expected in advanced cancer, where the basement membrane has disintegrated. However, the increased vascularization of the mid- and peripheral areas resulted in laminin staining of vessel basement membranes (FIG. 13c, bottom middle and right). The absence of laminin and collagen I in the core regions contribute to the soft phenotype of cancer cells. On the other hand, the increased staining towards the periphery marks the increase of stromal invasion related to stiffening in the respective regions. Moreover, immunostaining clearly shows that there is considerable tissue heterogeneity at late tumour stages that is reflected in the broad range of stiffness values.

Example 7

Figure 15:
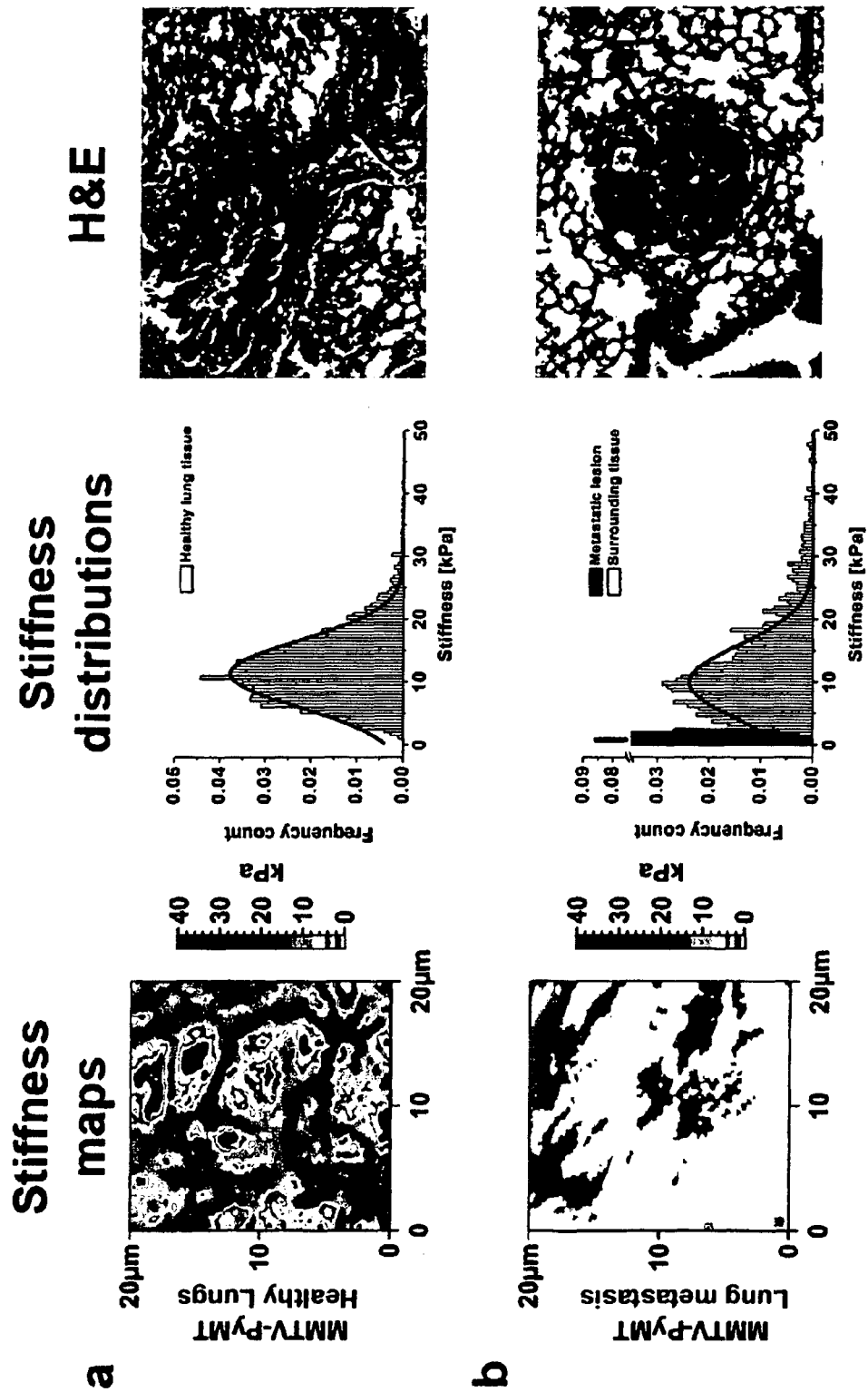
FIG. 15 shows the stiffness maps, stiffness distributions and histological assessments of healthy lungs (a) and lungs metastases (b) in MMTV-PyMT mice (scale bar=20 μm).

Soft and Hypoxic Cell Phenotype is Conducive to Lung Metastasis in the Mouse Model Next, the association between the softest cancer phenotypes with the ability to metastasize at distant sites, in particular to the lungs was examined. Healthy murine lungs contain high amounts of collagen IV and laminin and therefore exhibit a stiffer phenotype compared to mammary glands. AFM revealed that the average stiffness value is 11.01±5.19 kPa for healthy lung tissue (FIG. 15a, left, representative AFM stiffness map in the middle, Table 3) consisting of expanded alveolar and bronchial structures as well as blood vessels (FIG. 15a, right). At late stage of tumour progression, MMTV-PyMT mice develop lung metastasis. Consistently, stiffness measurements of lungs from late cancer stage mice demonstrate an extremely soft peak of 0.61±0.41 kPa ($P<0.0001$) (FIG. 15b, left, gray bars, representative AFM stiffness map in the middle, Table 3) that is absent in healthy lungs. Histological staining after AFM confirmed the presence of multiple metastatic lesions. Interestingly, compared to healthy lungs, the lung tissue surrounding metastases showed a flatter stiffness distribution with a mean stiffness at 8.19±4.94 kPa. The extensive hypoxia at advanced tumour stages alters collagen crosslinking in lungs. Conceivably, changes in the ECM of metastatic lungs are responsible for local variations of stiffness of lung tissue adjacent to metastases.

Metastasizing breast cancer cells in lungs exhibit soft phenotype similar to primary tumour (FIG. 15a) as shown by representative AFM stiffness map of healthy lungs and global stiffness profile (FIG. 15a, middle). Subsequent histological staining reveals normal epithelial morphology consisting of alveolar structures and bronchus (FIG. 15a, right). Representative AFM stiffness map of lungs (FIG. 15b, left) and global stiffness profile (middle) exhibited metastatic lesions. Histopathological analysis reveals the location of the metastatic cluster and the surrounding lung seemingly normal alveolar structures (FIG. 15b, right).

Figure 14:
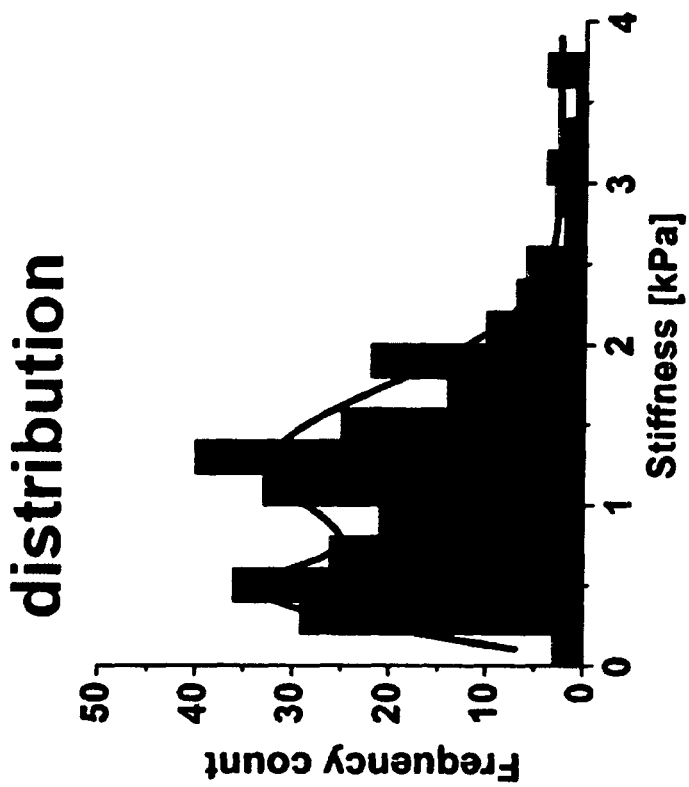
FIG. 14 shows the in situ nanomechanical characterization of cancer cells from MMTV-PyMT mice.
Figure 14:
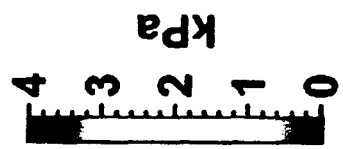
Figure 14:
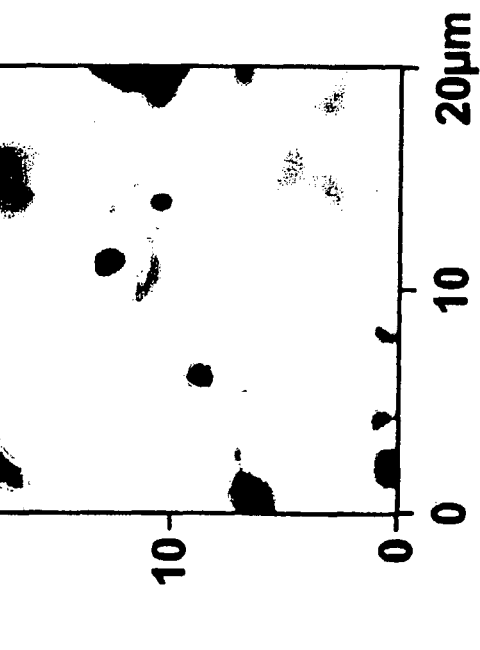

A representative AFM stiffness map (24×24) of one region reveals the nanomechanical heterogeneity amongst cancer cells (FIG. 14a). The stiffness distribution from a cellular region of the cancer biopsy reveals two peaks, first at the 0.45±0.15 kPa and the second at 1.26±0.43 kPa representing two distinct soft sub populations of cancer cells (FIG. 14b).

Poor differentiation as indicated by desmin and/or vimentin expression in cancer cells is another hallmark of aggressiveness. In contrast to normal and premalignant glands, where vimentin and desmin staining were tissue-specific, early cancer stage exhibits areas, where both vimentin and desmin are expressed in epithelial cancer cells. Finally in a late cancer, a distinct expression and distribution of vimentin and desmin was observed for soft cancer cells surrounding and intravasating blood vessels, which correlates well with the formation of soft metastatic cell clusters in lungs (FIG. 15b, left).

Example 8

Figure 16:
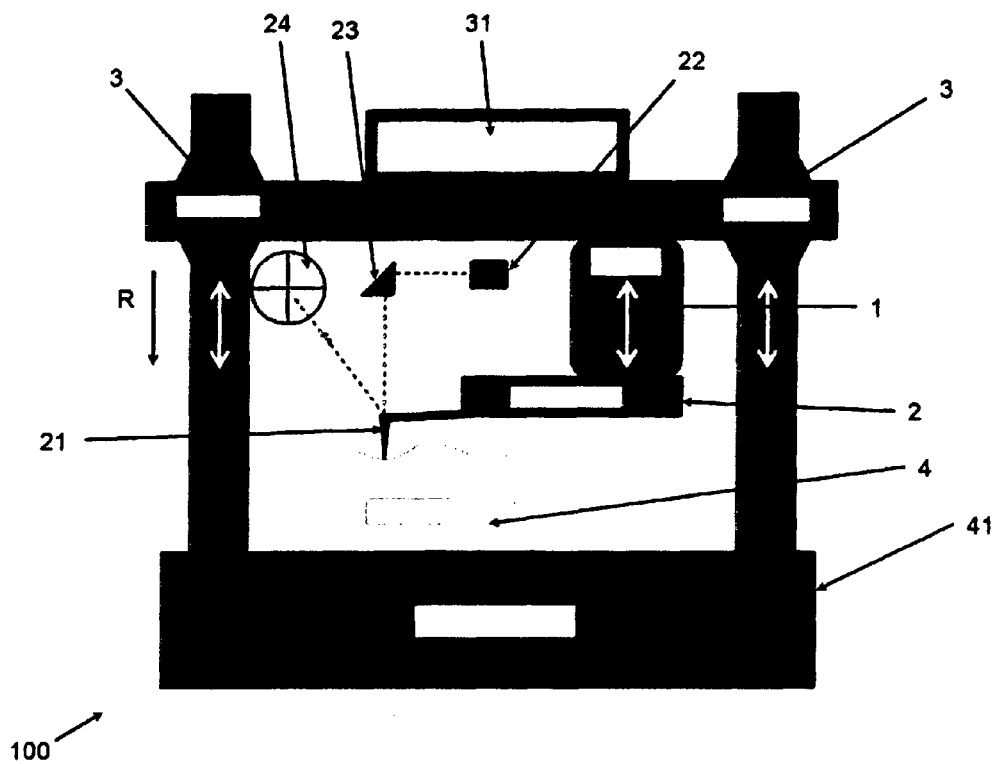
FIG. 16 shows a scheme of an AFM TOP-DOWN setup and with a vertical alignment component.

FIG. 16 shows an embodiment of the invention, wherein the piezo element 1 is directly coupled to the cantilever 2. In case of the piezo element 1 is maximally extended along the first direction R and the contact between cantilever tip 21 and sample 4 surface is loose, the controller 31 starts the external motors 3 (actuator) to lower the cantilever's tip 21 along the first direction R into the surface until desired extension of the piezo element 1 is reached. In case of the piezo element 1 is maximally retracted and the cantilever's tip 21 is indented into the sample surface 4 with an undesired force, the controller 31 starts the external motors 3 to lift the cantilever 2 along the first direction R to restore a desired extension of the piezo element 1.

Example 9

Figure 17:
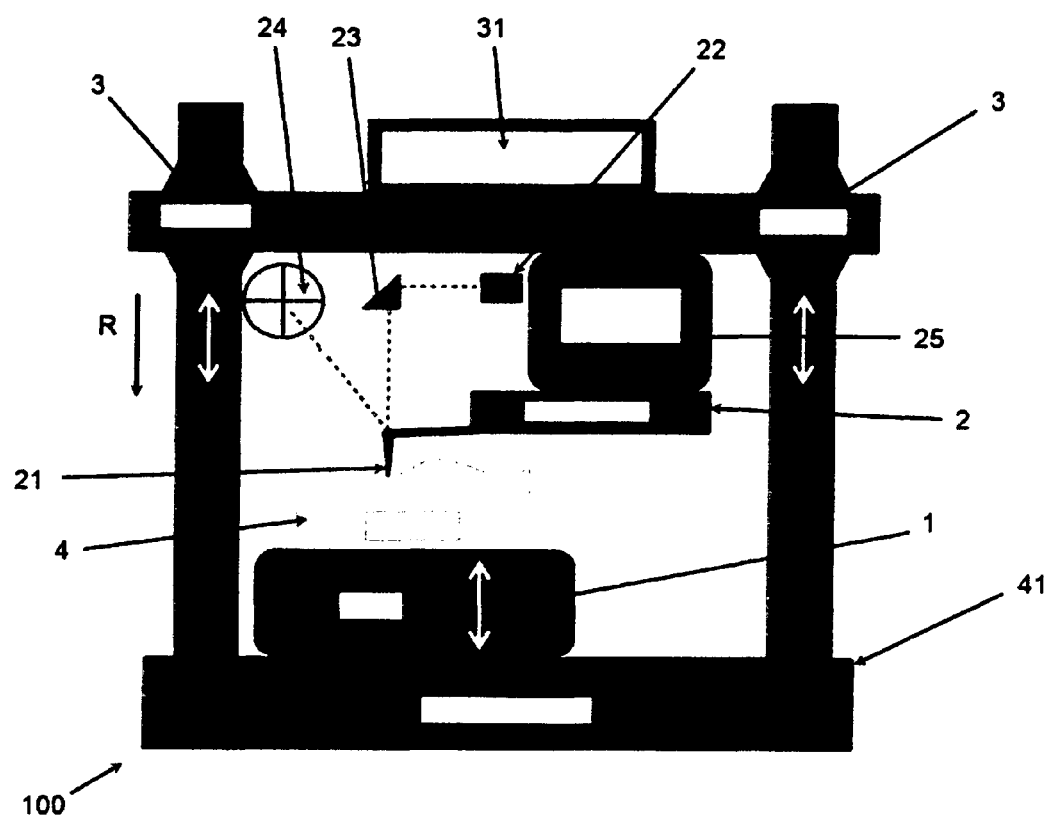
FIG. 17 shows a scheme of an AFM BOTTOM-UP setup and with a vertical alignment component.

FIG. 17 shows another embodiment of the invention, wherein the piezo element is directly coupled to the sample holder 41 and the cantilever 2 is attached to a cantilever holder 25.

Example 10

Figure 18:
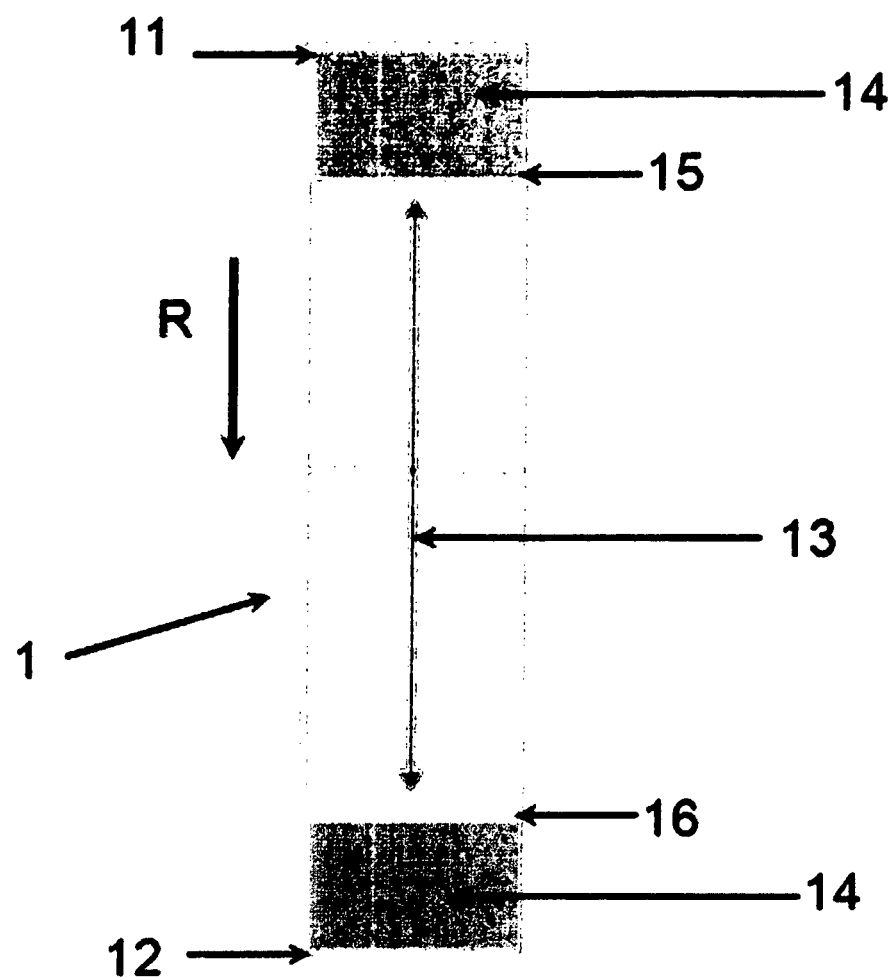
FIG. 18 shows a scheme of the piezo vertical movement.

FIG. 18 shows the scheme of the vertical piezo movement along the first direction R. The piezo element is characterized by a maximal extension 12 and a maximal retraction 11. Between these to states there is the working range of the piezo element that can be divided into the optimal working range 13 and the non-optimal working range. A first threshold 15 is situated at the border between the optimal working range 13 and the non-optimal working range 14 on the side of maximally retraction 11. A second threshold 16 is situated at the border between the optimal working range 13 and the non-optimal working range 14 on the side of maximally extension 12.

When the sample is getting too high and the piezo element 1 is retracted to the threshold 15, e.g. less than 20% of or 2 μm from its full extension range, the controller will activate the motors. The motors will move upwards and restore optimal working distance 13 of the piezo (e.g. between 20% and 80% of the maximum extension or between the initial 2 μm and the last 2 μm of the maximal extension) (FIG. 18). If the piezo is extended more than 80% or the last 2 μm of the full extension range at threshold 16, the controller will again start the motors, but this time they will move downwards to restore optimal piezo working distance 13 (FIG. 18). Typically, the cantilever is lowered or lifted by e.g. 3 μm if one is working with a piezo element of 15 μm full extension range. This value can be adjusted by the user to the given combination of AFM and motors.

Concept and Evidence

The complexity of cancer calls for improved biomarkers for the detection and analysis of the disease. The present invention has important implications for the use of nanomechanical properties as a novel biomarker for sensing and evaluating changes in native tumour tissues that can be translated into clinical settings.

The method of the invention clearly distinguishes between normal tissue, benign lesions such as fibroadenomas and cancer tissue. Although both types of tissue typically exhibit a uniform stiffness that is consistent with the respective homogenous morphological appearance, the stiffness of benign lesions is significantly higher than of normal mammary gland tissue. This apparent stiffening is most likely due to fibrocystic hyperplasia which results in a high content of fibrotic tissue that extends into and alters ductal myoepithelium. In contrast, nanomechanical AFM testing of mammary gland tissue samples obtained from MMTV-PyMT mice and human biopsies demonstrates, that malignant lesions are not characterized by a specific stiffness, but rather a radial gradient of stiffness that is related to the aggressive malignant phenotype.

The reports on tumour stiffness evaluation in the literature are diverging. Measurements performed on tissue biopsies by classical rheology led to the widely accepted notion that cancer tissue is generally stiffer than its surroundings. Similarly, unconfined compression testings have described tumours to be stiffer than normal tissues. In addition, a recent study showed that tissue fibrosis induced by collagen cross-linking, modulated integrin activity and elevated focal adhesions promotes stiffening of the tumour stroma. In contrast, a number of studies using different single-cell in vitro biomechanical assays report a decrease of stiffness in isolated cancer cells with increasing metastatic efficiency. For example, it was recently shown that metastatic cells isolated from cancer patients exhibit 70% lower stiffness than normal cells in the same sample. However, isolated and/or cultured cells lack the complex cell-cell and cell-matrix interactions that occur in tissues.

By testing fresh tissue samples both tissue architecture and ECM structure were retained. Moreover, the performed measurements represent a sampling of the entire tumour cross-section and thus account for the heterogeneity that is typical for tumours. Thus, AFM stiffness data partially reconcile these discrepancies in that they do not represent a single stiffness but rather a distinct nanomechanical signature. For example, similar to the increased stiffness measured by unconfined compression, AFM testing also revealed the stromal tumour tissue at the periphery to be relatively stiff; however, the underlying tumour is considerably softer. Because cancer is extremely diverse with respect to cell morphology and biochemistry, a common stiffness modulus for all tumour regions can hardly be expected. The data presented here offer a new paradigm for understanding how cancer stiffness and aggressive phenotype are influenced by tumour cell heterogeneity.

Hypoxia is amongst the microenvironmental conditions, which influence tumour progression by altering the expression of numerous gene products that are conducive to the survival and expansion of cancer cells in an oxygen deficient environment. These processes include angiogenesis, apoptosis, glycolysis, cell cycle control and most interestingly, migration. AFM measurements of MMTV-PyMT mammary tissue provide evidence, that hypoxia also modulates the nanomechanical properties of cancer tissue. In particular, hypoxia-related softening appears to promote an aggressive, metastatic phenotype. The made findings support the emerging concept that the tumour microenvironment regulates biophysical properties at the cell and/or tissue level. In the case of neoplastic mammary epithelial cells, the resulting downstream cellular response results in cell softening consistent with an increased metastatic potential. Consistently, cells with a hypoxic phenotype that were spreading from the core to the periphery in invasive cancer tissues resulted in a corresponding shift of the stiffness distribution. Although hypoxia was not directly measured in the human samples, the softness of the core suggests that these areas are also hypoxic.

Recently, it has been suggested that modification of the tumour microenvironment through ECM stiffening induced by lysyl oxidase (LOX) mediated collagen cross-linking promotes tumour invasiveness and metastasis. Hypoxia upregulates LOX expression and, most of all, its catalytic activity, which results in a degradation of collagen and drives poorly invasive breast cancer cells toward a more aggressive phenotype. It has been reported previously that hypoxia, through remodeling of ECM and the cytoskeleton, influences cell stiffness, and that these stiffness changes promote cell invasion and metastasis. A prominent degradation of collagen and fibronectin rather than an increase in fibrillar collagen was observed in regions with a high abundance of cancer cells. Similarly, MMP-dependent ECM degradation has been reported to accompany cancer progression. Data indicate a strong correlation between hypoxia, collagen degradation, and tissue softening in invasive carcinomas, although a ~15-fold increase in stiffness was measured in the tumour stroma adjacent to hypoxic cells. It is conceivable, that hypoxia-related tissue softening rather the ECM stiffening promotes tumour progression. The presence of lung metastases in MMTV-PyMT mice that have retained their hypoxic phenotype provides further support for this notion.

It is well known that hypoxia induces tumour angiogenesis via chemical and possibly mechanical signals. At the same time, hypoxia promotes tumour cell invasiveness which entails that cells cross the endothelial basement membrane during entry into and exit from blood vessels. At the transition from in situ to invasive carcinoma, structural degradation of the basement membrane is observed microscopically, which coincides with tumour cell invasion. Breaking of the basement membrane as the "last line of defense" before the tumour will spread most likely causes an additional increase in regional tissue softening and contributes to overall stiffness heterogeneity. Consistently, hypoxic cells were detected not only in the core but also near blood vessels in invasive carcinomas, adding to the characteristic heterogeneous stiffness pattern.

By making originally layered epithelial cells behave like motile fibroblasts, epithelialmesenchymal transition (EMT) and overexpression of mesenchymal markers are key elements in tumour progression. Expression of vimentin and desmin dramatically increased with the tumour progression both in MMTV-PyMT mice and human biopsies, thereby contributing to the heterogeneous stiffness phenotype. Coexpression of vimentin and desmin indicates cellular de-differentiation which might be conducive to adaptation to hypoxia. Expression and behavior of these markers during EMT on the other hand are affected by hypoxia. This might explain how the aggressive hypoxic phenotype is maintained even in well oxygenated environment such as blood vessels and lungs.

CONCLUSION

The data of the instant invention provide evidence that the soft phenotype plays a key role in cancer progression. Comparison of the nanomechanical signature of human tissue samples with the corresponding histopathological diagnosis proofs a high ratio of soft versus stiff regions to be an indication of a more aggressive phenotype.

Further immunohistochemical data (not shown) indicate that degradation and spatial reorganization of ECM components are associated with tumour progression. At the same time, structural changes of SM-actin, vimentin and desmin within the localized primary tumour indicate significant changes in the cytoarchitecture. As the tumour progresses the structural heterogeneity further increases, it is evident that changes in ECM organization and cytoarchitecture affect the nanomechanical response of cells and thus tumour progression is characterized by an increase in the stiffness heterogeneity.

This is in good agreement with the bimodal stiffness distribution measured in carcinomas by AFM. Furthermore, laminin is markedly disorganized and reveals that the loss of epithelial polarity is consistent with malignancy and invasiveness.

TABLE 1

| | | AFM stiffness values ± SD [kPa] | | | | |
|---|---|---|---|---|---|---|
| Case no. | Age/sex | Peak 1 | Peak 2 | Peak 3/other | Corresponding histopathological diagnosis | Grade (g) |
| 1 | 20/female | 1.19 ± 0.82 | — | — | Healthy | — |
| 2 | 31/female | 1.13 ± 0.78 | — | — | Healthy | — |
| 3 | 34/female | 1.17 ± 0.67 | — | — | Healthy | — |
| 4 | 50/female | 1.23 ± 0.24 | — | — | Healthy | — |
| 5 | 53/female | 1.31 ± 0.76 | — | — | Healthy | — |
| 6 | 55/female | 1.83 ± 1.13 | — | — | Healthy | — |
| 7 | 61/female | 1.33 ± 0.32 | 2.63 ± 2.06 | — | Fibroadenoma with ductal hyperplasia | — |
| 8 | 47/female | — | 1.91 ± 0.99 | — | Fibroadenoma | — |
| 9 | 48/female | — | 3.94 ± 1.49 | — | Fibroadenoma | — |
| 10 | 49/female | — | 3.41 ± 1.97 | — | Fibroadenoma | — |
| 11 | 56/female | — | 3.68 ± 1.92 | — | Fibroadenoma | — |
| 12 | 63/female | 0.56 ± 0.24 | 1.82 ± 0.96 | 7.71 ± 4.55 | Invasive ductal carcinoma | 3 |
| 13 | 44/female | 0.61 ± 0.21 | 1.54 ± 0.30 | — | Oncocytic invasive carcinoma | 2 |
| 14 | 45/female | 0.46 ± 0.21 | 1.19 ± 0.84 | — | Invasive ductulo-lobular carcinoma | 2 |
| 15 | 61/female | 0.75 ± 0.22 | 1.64 ± 0.78 | ill-defined exponential decline | Invasive ductal carcinoma | 2 |
| 16 | 73/female | 0.73 ± 0.34 | 1.47 ± 1.67 | — | Invasive ductal carcinoma with lobular growth pattern | 2 |
| 17 | 83/female | 0.63 ± 0.50 | — | ill-defined exponential decline | Apocrine carcinoma | 2 |
| 18 | 61/female | 0.57 ± 0.16 | 1.99 ± 0.73 | 5.75 ± 1.62 | Invasive ductal carcinoma | 1 |
| 19 | 69/female | 0.66 ± 0.31 | 1.71 ± 1.41 | — | Invasive ductal carcinoma | 1 |
| 20 | 79/female | 0.53 ± 0.23 | 1.81 ± 0.42 | 7.41 ± 2.49 | Invasive lobular carcinoma | 1 |
| 21 | 95/female | 0.31 ± 0.12 | — | 8.45 ± 1.77 | Invasive ductal carcinoma | 1 |

TABLE 2

| Mouse (sample no.) | AFM stiffness values [kPa] ± SD Peak 1 | AFM stiffness values [kPa] ± SD Peak 2 | Corresponding histopathological diagnosis |
|---|---|---|---|
| 1 | 1.148 ± 0.482 | — | Normal |
| 2 | 1.075 ± 0.622 | — | Normal |
| 3 | 1.021 ± 0.524 | — | Normal |
| 4 | 0.983 ± 0.860 | — | Normal |
| 5 | 1.149 ± 1.275 | — | Normal |
| 6 | 0.959 ± 0.931 | — | Normal |
| 7 | 0.956 ± 0.260 | — | Normal |
| 8 | 1.124 ± 0.503 | — | Normal |
| 1 | 1.023 ± 0.054 | 1.449 ± 0.693 | Premalignant |
| 2 | — | 2.437 ± 0.844 | Premalignant |
| 3 | 1.012 ± 0.434 | 2.046 ± 0.679 | Premalignant |
| 4 | 1.265 ± 0.549 | 1.963 ± 1.382 | Premalignant |
| 5 | 1.612 ± 0.244 | 2.166 ± 1.042 | Premalignant |
| 6 | 1.579 ± 0.973 | — | Premalignant |
| 7 | 1.568 ± 0.648 | — | Premalignant |
| 1 | 0.591 ± 0.178 | 1.404 ± 0.556 | Early cancer |
| 2 | 0.467 ± 0.158 | 1.496 ± 0.748 | Early cancer |
| 3 | 0.721 ± 0.068 | 4.195 ± 2.837 | Early cancer |
| 4 | 0.443 ± 0.112 | 1.069 ± 0.512 | Early cancer |
| 5 | 0.771 ± 0.152 | 1.446 ± 0.879 | Early cancer |
| 6 | 0.498 ± 0.192 | 1.554 ± 0.895 | Early cancer |
| 7 | 0.521 ± 0.180 | 1.414 ± 0.812 | Early cancer |
| 1 | 0.626 ± 0.197 | 3.171 ± 2.312 | Late cancer |
| 2 | 0.723 ± 0.277 | 2.422 ± 0.701 | Late cancer |
| 3 | 0.503 ± 0.032 | 5.081 ± 2.746 | Late cancer |
| 4 | 0.650 ± 0.131 | 5.279 ± 3.122 | Late cancer |
| 5 | 0.767 ± 0.041 | 4.493 ± 3.060 | Late cancer |
| 6 | 0.567 ± 0.223 | 2.636 ± 1.449 | Late cancer |
| 7 | 0.744 ± 0.301 | 3.451 ± 1.701 | Late cancer |
| 8 | 0.699 ± 0.155 | 4.404 ± 1.001 | Late cancer |

TABLE 3

| Mouse (lung no.) | AFM stiffness values [kPa] ± SD Normal | AFM stiffness values [kPa] ± SD Metastasis | AFM stiffness values [kPa] ± SD Surrounding |
|---|---|---|---|
| 1 | 9.917 ± 4.753 | | |
| 2 | 11.302 ± 5.246 | | |
| 3 | 11.334 ± 5.808 | | |
| 4 | | 0.776 ± 0.689 | 9.723 ± 5.215 |
| 5 | | 0.588 ± 0.377 | 10.685 ± 6.763 |
| 6 | | 0.777 ± 0.880 | 8.354 ± 4.548 |

List of reference elements

| 100 | Atomic force microscope of invention |
|---|---|
| 1 | Piezo element |
| 11 | Maximally retraction |
| 12 | Maximally extension |
| 13 | Optimal working range |
| 14 | Non-optimal working range |
| 15 | Threshold to lift the cantilever |
| 16 | Threshold to lower the cantilever |
| 2 | Cantilever |
| 21 | Cantilever's tip |
| 22 | Laser |
| 23 | Mirror |
| 24 | Photodiode |
| 25 | Cantilever holder |
| 3 | Motor |
| 31 | Controller |
| 4 | Sample |
| 41 | Sample holder |
| R | First direction |

The invention claimed is:

1. A method for classifying a tissue biopsy sample obtained from a tumour, comprising
    determining, by a scanning probe microscope, the stiffness values for a plurality of points on said sample with a spatial resolution of at least 100 µm, resulting in a stiffness distribution, and
    classifying assigning said sample according to the determined stiffness values,
wherein
    a sample showing an at least bimodal stiffness distribution is classified as a malignant tumour, wherein said at least bimodal stiffness distribution is characterized by a first peak exhibiting an at least two-fold higher stiffness value than a second peak.

2. The method of claim 1, wherein said plurality of points is arranged as a grid of $n_1$ by $n_2$ points, said grid defining an area.

3. The method of claim 2, whereby said stiffness values of at least two different areas of said same sample are determined, and the distance between the geometrical centres of said areas is a multiple of said spatial resolution of at least 10.

4. The method of claim 1, wherein a sample showing a unimodal stiffness distribution is classified as a non-malignant tumour.

5. The method of claim 1, wherein said tissue biopsy sample is a cylindrical or prismatic biopsy with a diameter of at least 7 µm.

6. The method of claim 1, wherein said tumour is a human mammary carcinoma or a lymph node, lung, bone, liver or brain metastasis.

7. The method of claim 1, wherein said stiffness values are determined under physiological conditions.

8. The method of claim 1, wherein the stiffness of a mammary tissue biopsy sample is determined and wherein
    a sample showing a stiffness distribution characterized by a peak between 1.1 kPa and 1.5 kPa is classified as normal mammary tissue,
    a sample showing a stiffness distribution characterized by a peak between 1.9 kPa and 3.7 kPa is classified as a benign lesion, and
    a sample showing a stiffness distribution characterized by peaks between 0.31 kPa and 0.75 kPa and at a value larger than 1.2 kPa is classified as a malignant tumour.

9. The method of claim 8, wherein a sample showing a stiffness distribution characterized by peaks between 0.31 kPa and 0.75 kPa and between 1.2 kPa and 2.0 kPa is classified as a malignant tumour.

10. The method of claim 1, wherein said scanning probe microscope comprises
    a probe with a tip for interacting with said sample, and
    a nanoscanner for retaining said sample or said probe,
wherein
    the extension of said nanoscanner along a first direction, along which said tip is moved towards said sample, is monitored, and
    a level of said probe along said first direction is adjusted by means of an additional actuator when said nanoscanner exhibits an extension below or above a threshold value.

11. The method of claim 10, wherein said adjusting is performed by lowering or lifting said probe or by lowering or lifting said sample.

12. The method of claim 11, wherein said level is adjusted when said nanoscanner exhibits an extension lower than 20% or higher than 80% of its maximal extension.

13. The method of claim 11, wherein said level is adjusted by lowering or lifting said probe or said sample by 10 to 30% of the maximal extension of said nanoscanner.

14. A system for classifying a tumour tissue biopsy sample, comprising
- a device, particularly an atomic force microscope, for determining stiffness values with a resolving power of at least 1 μm, and
- a programmed microprocessor, wherein
said programmed microprocessor is equipped and designated to run the method of claim 1.

15. The system of claim 14, wherein said atomic force microscope comprises:
- a probe having a tip for interacting with a sample, wherein said probe is configured to move said tip towards said sample along a first direction, and
- a nanoscanner for retaining said sample or said probe, characterized in that
said device comprises a means for monitoring the extension of said piezo element along said first direction, an actuator for adjusting a level of said probe along said first direction and a controller for controlling said actuator, wherein said controller is configured to control said actuator so as to adjust said level of said probe, when said nanoscanner exhibits an extension below or above a threshold value.

16. The method of claim 1, wherein the scanning probe microscope is an atomic force microscope.

* * * * *